United States Patent [19]

Marshall et al.

[11] Patent Number: 4,941,093
[45] Date of Patent: Jul. 10, 1990

[54] SURFACE EROSION USING LASERS

[75] Inventors: John Marshall, Farnborough; Anthony L. Raven, Royston; Walter T. Welford, London; Karen M. M. Ness, Royston, all of Great Britain

[73] Assignee: Summit Technology, Inc., Mass.

[21] Appl. No.: 905,156

[22] Filed: Sep. 9, 1986

Related U.S. Application Data

[63] Continuation-in-part of Ser. No. 869,335, Jun. 2, 1986, abandoned.

[30] Foreign Application Priority Data

Sep. 12, 1985 [GB] United Kingdom ............... 8522630
Feb. 21, 1986 [GB] United Kingdom ............... 8604405

[51] Int. Cl.$^5$ .............................................. A61B 17/00
[52] U.S. Cl. ........................... 364/413.01; 219/121.61; 606/5
[58] Field of Search .................. 364/413, 413.01; 128/303.1; 219/121 L, 121 LP, 121 LG, 121 LN, 121 LR, 121.61; 606/3-6

[56] References Cited

U.S. PATENT DOCUMENTS

| | | | |
|---|---|---|---|
| 3,941,973 | 3/1976 | Luck, Jr. et al. | 219/121.68 |
| 4,409,979 | 10/1983 | Roussel et al. | 219/121 L |
| 4,623,776 | 11/1986 | Buchroeder et al. | 219/121 LR |
| 4,628,461 | 12/1986 | Dewey | 128/303.1 |
| 4,648,400 | 3/1987 | Schneider | 128/303.1 |
| 4,665,913 | 5/1987 | L'Esperance, Jr. | 219/121 LP |

Primary Examiner—Jerry Smith
Assistant Examiner—Kim Thanh Tbui

[57] ABSTRACT

Laser apparatus for eroding a surface comprises means to select and control the shape and size of the area irradiated by each pulse of laser energy without varying the energy density of the beam. By varying the size of the irradiated area between pulses, some regions of the surface may be eroded more than others and so the surface may be reprofiled. The method and apparatus are suitable, inter alia, for removing corneal ulcers and reprofiling the cornea to remove refractive errors and also for reprofiling optical elements. In one embodiment the beam from the laser enters an optical system housed in an articulated arm and terminating in an eyepiece having a suction cup for attachment to an eye. The optical system includes a beam forming arrangement to correct an asymmetric beam cross-section, a first relay telescope, a beam dimensional control system and a second relay telescope. The beam dimension control system has a stop with a shaped window or a shaped stop portion and movable axially along a converging or diverging beam portion. An alternative beam dimension control system has a stop with a shaped window and positioned between coupled zoom systems. Mirrors, adjustable slits and refractive systems may also be used. The laser is preferably an ArF Excimer laser. The apparatus may include a measurement device to measure the surface profile, and a feedback control system to control the laser operation in accordance with the measured and desired profiles.

44 Claims, 9 Drawing Sheets

SURFACE EROSION USING LASERS

CROSS REFERENCE TO RELATED APPLICATIONS

This application is a continuation-in-part of Application Ser. No. 869335 filed June 2nd 1986 and now abandoned.

FIELD OF THE INVENTION

This invention concerns apparatus and methods employing lasers, particularly pulsed lasers, for eroding surfaces, such as to shape them.

BACKGROUND TO THE INVENTION

Methods for using a laser source to erode surfaces of workpieces are known.

It is an object of the present invention to provide an improvement in such methods and apparatus whereby such techniques can be applied to sensitive surfaces and in particular to objects in which it would be undesirable to affect underlying layers.

In the field of medicine a known technique for the treatment of certain forms of myopia is surgically to remove a segment of the collagen sub-surface layer of the eye, to reshape the removed segment as by surgical grinding, and to restore the reshaped segment in the eye. The eye heals by reformation of the outer cellular layer over the reshaped collagen layer. Alternatively a layer of the cornea is opened up as a flap, an artificial or donor lenticular implant is inserted under the flap, and the flap is sutured up again.

It is a further object of this invention to provide an improved and less traumatic method and apparatus for reshaping the cornea of the eye.

It is also known to perform corneal transplants in which a section of the cornea from a donor eye is transplanted to the eye of a patient. The transplanted donor corneal insert has to be stitched to the patient's eye, and quite commonly accidental overtightening of some of the stiches introduces refractive errors into the cornea following the operation. At present, there are two methods of removing these refractive errors. For both it is necessary to wait until the patient's eye has healed. In one method the transplant operation is then performed again. In the other method, relaxing incisions are made in the cornea to change its shape.

It is a further object of this invention to provide an improved and less traumatic method and apparatus for remedying refractive errors introduced during corneal transplant operations.

It is known to treat corneal ulcers by scraping the ulcerous material off the cornea. However, this tends to spread the ulcerous cells. Additionally, the scraping tends not to leave a smooth underlying surface, and the corneal surface layer which reforms subsequently may not be entirely clear and may also tend to become ulcerated again.

It is a further object of this invention to provide a method and apparatus for removing corneal ulcers which does not spread ulcerous cells across the eye and which leaves a smooth surface after removal of the cells.

The use of a laser beam as a surgical tool for cutting incisions, a so-called "laser scalpel", has been known for some time (see for example U.S. Pat. No. 3,769,963 to Goldman L et al). In 1980, a study was made of the damage which might be inflicted on the corneal epithelium by exposure to recently developed Excimer lasers (see Taboada et al "Response of the Corneal Epithelium to KrF excimer laser pulses" Health Physics 1981 Volume 40 pp677-683). At that period, surgical operations on the cornea were commonly carried out using diamond or steel knives or razors, and further such techniques were still being studied (see for example Binder et al "Refractive Keratoplasty" Arch. Ophthalmol. May 1982 Vol 100 p 802). The use of a physical cutting tool in corneal operations, and the insertion of an implant under a flap, continue to be widely practiced and techniques further developed up to the present day (see for example "Refractive Keratoplasty improves with Polysulfone, Pocket Incision" Ophthalmology Times, July 1, 1986).

It has been suggested in European Patent Application No. 0151869 of L'Esperance, to perform controlled ablative photodecomposition of one or more selected regions of a cornea using a scanning action on the cornea with a beam from an Excimer laser. Because of the scanning action, it is necessary for L'Esperance to bring his laser beam to a small spot, typically a rounded-square dot of size 0.5 mm by 0.5 mm. There is no suggestion that the spot size or shape should be varied, or controlled other than to produce the above-mentioned standard size and shape, and indeed, in the L'Esperance system any such spot size variation would be highly undesirable since the effects of the laser beam on the cornea are intended to be controlled by controlling the scanning path.

L'Esperance suggests that myopic and hyperopic conditions can be reduced by altering the curvature of the outer surface of the cornea by repeatedly scanning the cornea with an Excimer laser beam having this standard, small spot size but varying the field which is scanned during successive scans, so that some areas of the cornea are scanned more often than others. In this way it is claimed that the surface can be eroded by different amounts depending on the number of times they are scanned by the spot. L'Esperance also suggests making uniform-depth removals of material from the cornea to provide a recess for the reception and location of a corneal transplant. Additionally, he suggests that certain severe myopic and hyperopic conditions may be treated with a reduced removal of tissue by providing the outer surface of the cornea with a new shape having Fresnel-type steps between areas of the desired curvature.

In practice, complex apparatus is required to cause a laser beam to scan with the precision required if the eroded surface is to be smooth. Thus if successive sweeps of a scan overlap there will be excessive erosion in the overlap area, whereas if they fail to meet a ridge will be left between the sweeps. The compression of the Excimer laser beam to a small spot will increase the beam energy density, which will tend to exacerbate these problems. It is not clear that L'Esperance has found a suitable scanning system, since in one embodiment he attempts to control the laser beam by a magnetic field.

Additionally, the scanning method is inherently time-consuming even with highly refined techniques and apparatus, since the laser beam is only eroding a very small part of the total area to be treated at any given moment.

Furthermore, such a scanning system will tend to cause rippling effects on relatively soft materials such as corneal tissue.

It is therefore a further object of the present invention to provide a method and apparatus for eroding a surface using a laser which does not require scanning of the area of the surface to be eroded.

SUMMARY OF THE INVENTION

According to one aspect of the present invention there is provided a laser system for eroding a surface comprising laser means and locating means for locating the surface accurately relative to the laser means, the laser means being operable to deliver pulses of laser energy to a surface located by the locating means to erode it, and having means to control and vary the size of the area on the surface to which each pulse of laser energy is delivered.

According to another aspect of the invention there is provided a method of eroding a surface by laser energy, in which a surface is located accurately relative to laser means operable to deliver pulses of energy to the surface and the size of the area on the surface to which the pulses are delivered is adjusted in a controlled manner thereby to select the size of the area eroded by each pulse prior to the operation of the laser.

Preferably, it is also possible to control and adjust the shape of the area on the surface to which the pulses are delivered.

The method and apparatus of the present invention may be applied to alter the contours of a surface thereby to change its shape. Accordingly, the method of the present invention may include the step of varying in a controlled manner during operation of the laser the size and preferably the shape of the area to be eroded by each pulse so as to produce a desired change in the shape of the surface by erosion.

According to a further aspect of the invention's, in a laser system for eroding and thereby shaping or reprofiling a surface there is provided:

(1) means for accurately locating the surface to be eroded relative to an optical axis (or vice versa);

(2) a beam delivery system for relaying energy from a laser light source onto the surface along the said optical axis;

(3) a laser light source, power supply and associated control circuit means for generating pulses of laser energy for application to the surface; and (4) means for controlling the area over which the pulses of laser energy are applied to the surface, there's by to cause greater or lesser ablation of the irradiated regions.

According to another aspect of the invention, a method of eroding a surface of an object comprises the steps of:

(1) locating the object accurately relative to a laser source, (2) pulsing the laser source so that energy therefrom falls on the surface of the object, and (3) controlling the output of the laser so as to vary the area over which the energy is incident during the emission of a plurality of pulses, to thereby selectively expose areas of the surface to a greater or lesser extent and thereby to obtain a desired erosion profile in the surface.

Where the surface is large, the apparatus is conveniently located relative thereto.

Where the surface is on a relatively small object, the latter is more conveniently located relative to the optical axis.

According to a preferred feature of the invention, where the surface comprises a layer of a material which is different from that below the surface layer and it is desired not to affect the underlying layers the laser wavelength is selected so that the laser energy incident on the surface is absorbed by the material forming the said surface layer so that there is little or no energy remaining to penetrate and affect the underlying material.

Preferably the laser is pulsed repeatedly and using an iris diaphragm, optical stops, mirrors, beamsplitters and other similar devices, the pulses of energy are directed towards the surface either in their entirety or partially, and/or towards a selected region or selected regions of the surface, so that, over a period of time, different regions of the surface are exposed to different quantities of energy from the laser source, so as to produce differential erosion of the surface.

Where a required change comprises an increase in the concavity (or a decrease in the convexity) in the surface of an object and the area over which the energy can be dissipated can be made at least equal to the area over which the change is to be effected, the latter may be eroded to effect such a change by exposing the surface to a succession of pulses of light energy whilst controlling the area of illumination produced by each pulse, so as to successively reduce this area.

In this way the central region will be exposed to more energy than the peripheral regions of the area concerned so that greater erosion occurs in the central region relative to the peripheral regions thereof, to thereby increase the concavity of a concave surface, produce a concave erosion of a flat surface or a reduction in convexity of a convex surface.

Conversely, if an increase in convexity (or a decrease in concavity) is required, the opposite approach is used, and the peripheral regions are exposed to a greater extent than the central region, thereby leaving a "hill" in the middle of the region to which the laser energy is applied.

In a particularly preferred arrangement of the invention particularly applicable to the profiling of lenses, mirrors, or other optical elements, a measuring device is included within the apparatus for measuring a parameter which is a function of the surface shape of the optical element such as refractive power or surface curvature, means is provided for receiving an input defining a desired value for the parameter such as a keyboard and a random access memory device, comparison means is included for comparing the measured value of the parameter with the desired value, and control signal generating circuit means is provided for generating control signals for the laser from the feedback signal obtained from the comparison, the control signals serving inter alia, to determine the area over which the laser pulses are effective, thereby to obtain the desired value of the parameter of the optical element.

Typically the comparison means and the control signal generating circuit means are provided by a computer system incorporating the Random Access Memory. The input may specify the desired value of the parameter directly, or, it may define it by specifying a desired value for another, related, parameter from which the desired value of the first parameter can be derived.

In a preferred method, the laser light source is pulsed so as to produce pulses of light having substantially constant energy density, so that a known depth of surface material will be eroded for each pulse. By using relatively low power, only a microscopically thin layer of material will be removed in response to each pulse. By continual monitoring and feedback, a very accurate profiling of the surface can be achieved.

The invention is of particular application to the reprofiling of the surface of the cornea of the eye.

By reference to the surface of an object is meant the surface which is from time to time exposed. Thus in reprofiling a cornea, a lasting change in shape is only obtained if layers of the corneal stroma are removed. To this end the overlying epithelium of the cornea must be removed prior to reprofiling and may for example be ablated by the initial pulses of the laser, whereafter the laser can erode the exposed surface of the cornea to effect a permanent change of shape, the overlying epithelium re-forming by the natural healing process, after erosion.

According therefore to a further aspect of the invention, a method of reprofiling the surface of the cornea of the eye comprises the steps of:

(1) fixing the eye relative to a laser source, (2) pulsing the laser source so that light therefrom falls on the surface of the cornea, and (3) controlling the light from the laser so as to vary the area over which the light is incident during the emission of a plurality of the pulses, thereby selectively exposing areas of the surface to a greater or lesser extent and obtaining a desired erosion profile in the surface.

According to a still further aspect of the present invention, there is provided a method of eroding an area of the surface of the cornea of the eye in which the eye is fixed relative to laser means operable to deliver pulses of laser energy to the surface of the cornea, the size and preferably the shape of the area on the surface of the cornea to which the pulses are delivered is adjusted in a controlled manner thereby to select the size and preferably the shape of the area eroded by each pulse and the laser is then operated.

According to a preferred feature of the invention, the laser wavelength is selected so that the laser energy incident on the surface of the cornea is absorbed by the material forming the cornea so that there is little or no energy remaining to penetrate and affect the underlying material of the eye.

The invention thus provides a method and apparatus for reprofiling the surface of the cornea for correcting refractive errors in the eye (such as myopia, hyperopia and astigmatism, etc) which uses a pulsed laser source and a beam delivery system by which the size and shape of the laser beam at the surface of the cornea can be varied.

Additionally, the reprofiling method and apparatus of the present invention may be used for correcting refractive errors in the eye following a corneal transplant operation. Thus, if the transplant operation introduces refractive errors (as, for example, by the accidental over-tightening of one or more stitches), the refractive errors may be removed by reprofiling the surface of the cornea instead of by performing the transplant operation again or making relaxation incisions.

Furthermore, the method and apparatus of the present invention for eroding the surface of the cornea may be used to remove corneal ulcers. By controlling the size and preferably the shape of the area eroded by any one pulse, it is possible to limit the eroded material substantially entirely to each region of ulcerous material to be removed. Since there is no physical scraping of the ulcerous material across the eye, the ulcerous cells are not spread by this process. Additionally, with some laser wavelengths (for example 193 nm), the surface remaining after ablation is smooth, minimising optical defects in the cornea after healing, and reducing the liklihood of the re-occurrence of the ulcer.

An automatic feedback control system may be provided in which the output from a measuring device for measuring the shape or an optical property of the eye is used to control the delivery of pulses of laser energy. Alternatively, the desired surface profile may be obtained through erosion by a successive approximation technique. In this technique, a measuring device is used to determine the change it is desired to make in the profile of the surface. Pulses of laser energy are delivered to the surface so as to bring about slightly less than the desired alteration. The measuring device is used again to determine the correction now needed to reach the desired profile, and further pulses of laser energy are provided accordingly to produce slightly less than the total calculated correction. This process is repeated until the eroded surface acquires the desired profile to a suitable degree of accuracy.

Suitable measurement devices, commonly called keratometers, are known and commercially available. Examples of such devices are the "Photokeratoscope" manufactured by the Sun Contact Lens Company of Kyoto, Japan and the "Corneascope" manufactured by International Diagnostic Instruments Limited, Broken Arrow, OK, USA (See S. D. Klyce, "Computer Assisted Corneal Topography", Invest. Ophthalmol. Vis. Sci. 25:1426–1435, 1984 for a comparison of these instruments and a method of using the "Photokeratoscope").

In order to locate the eye relative to the laser means, conventional suction rings or cups may be used, such as those provided by Steinway Instruments of San Diego, Calif. USA. These are normally applied to the white (sclera) region of the eye and connected to a low suction pressure sufficient to clamp the cup to the eye but not so great that the cornea is distorted. The cup may then be fixed to further apparatus (in the present case, this will normally be the (optical system of the laser) which will thereby be located accurately with respect to the eye. The use of such a cup to locate a microkeratome blade relative to an eye is shown on page 39 of Ophthalmology Times of July 1, 1986, and such a procedure is well known in the art.

Examples of lasers which may be used are an Excimer laser, an HF laser, and a pulsed $CO_2$ laser. An ArF Excimer laser is presently preferred for corneal ablation. In medical uses such as corneal ablation, it is preferred to use an Excimer laser which is designed for medical applications, such as the EXCIMED system manufactured by Summit Technology Inc; of Watertown, Mass. USA.

When such lasers are used to irradiate the cornea, the thin layer is ablated from the surface of the cornea in the irradiated regions.

The pulse repetition rate for the laser may be chosen to meet the needs of each particular application. Normally the rate will be between 1 and 500 pulses per second, preferably between 1 and 100 pulses per second. When it is desired to vary the beam size, the laser pulses may be stopped. Alternatively, the beam size may be varied while the pulses continue. If a measurement device is used to monitor the erosion progress and control the laser system automatically, the beam size may be varied continuously at a controlled rate without interrupting the pulses.

Suitable irradiation intensities vary depending on the wavelength of the laser, and the nature of the irradiated object. For any given wavelength of laser energy applied to any given material, there will typically be a threshold value of energy density below which significant erosion does not occur. Above the threshold density, there will be a range of energy densities over which increasing energy densities give increasing depths of erosion, until a saturation value is reached. For increases in energy density above the saturation value, no significant increase in erosion occurs.

The threshold value and the saturation value vary from wavelength to wavelength of laser energy and from material to material of the surface to be eroded, in a manner which is not easily predictable. However, for any particular laser and any particular material, the values can be found readily by experiment. For example, in the case of eroding corneal stroma (collagen sub-layer) by energy of wavelength 193 nm (the wavelength obtained from an ArF Excimer laser), the threshold value is about 50 mJ per $cm^2$ per pulse, and the saturation value is about 250 mJ per $cm^2$ per pulse. There appears to be little benefit in exceeding the saturation value by more than a small factor, and suitable energy densities at the corneal surface are 50 mJ per $cm^2$ to one J per $cm^2$ per pulse for a wavelength of 193 nm.

The threshold value can vary very rapidly with wavelength, and at 157 nm, which is the wavelength obtained from an $F_2$ laser, the threshold is about 5 mJ per $cm^2$ per pulse. At this wavelength, suitable energy densities at the corneal surface are 5 mJ per $cm^2$ to one J per $cm^2$ per pulse.

Most preferably, the laser system is used to provide an energy density at the surface to be eroded of slightly less than the saturation value. Thus, when eroding the cornea with a wavelength of 193 nm (under which conditions the saturation value is 250 mJ per $cm^2$ per pulse), it is preferable to provide to the cornea pulses of an energy density of 100 to 150 mJ per $cm^2$ per pulse.

Typically, a single pulse will erode a depth in the range 0.1 to 1 micrometer of collagen from the cornea.

The shape of the ablated region can be defined by irradiating the object (eg a cornea) through an aperture which may be of adjustable dimensions and shape, and/or by using an optical stop which may also be adjustable in size and shape.

To achieve a change in the refractive profile of the object such as the cornea of an eye, the object is irradiated by a pattern of light which varies with time so that different regions thereof receive different numbers of pulses and are therefore eroded to a different extent.

If a circular iris is placed in the beam directed at an object, such as the cornea of an eye, and the iris is expanded (ie opened) while the pulses continue to be delivered, the central region of the object will, after a given period of time, have received more pulses (and will consequently have been eroded to a greater extent) than the surrounding annular exposed regions.

By controlling the number of pulses emitted for each setting of the aperture and controlling the aperture size, the actual profile of the eroded surface of the object can be very closely controlled.

In practice, iris diaphragms do not always maintain the shape of their aperture constant as they vary in size, and additionally the range of shapes available for iris diaphragms is limited. An alternative system, which is presently preferred, is to pass a collimated beam of laser energy through an optical system which causes the beam to have a region of divergence, a region of convergence, or both, before it is re-collimated. A beam-shaping stop is arranged to move along the beam axis in a region of convergence or divergence. The stop may have a beam-shaping aperture or window to provide a variable size shaped beam. Alternatively, it may have a shaped stop portion where the beam is to be provided with a region of reduced or zero illumination of variable size.

Combinations of apertures and stop portions may be provide if a more complex beam shape is required.

For convenience, the following description is in terms of a stop having an aperture, but other types of stop will function in an analagous manner.

As such a stop is moved along the axis of the beam, the beam diameter at the position of the stop will vary. Thus, when the stop is at one end of its range of travel (where the beam diameter is smallest), all (or a relatively large portion) of the beam will pass through the aperture, whereas when the stop is at the other end of its range of travel (maximum beam diameter), only a relatively small portion of the beam will pass through the aperture. Only that portion of beam which passes through the aperture is re-collimated, and thus moving the stop axially of the beam will vary the size of the collimated output beam. The shape of the collimated output beam will be governed by the shape of the aperture in the stop. Since the portion of the laser beam passing through the aperture is unaffected by it, the stop has no effect on the energy density of the beam but merely on its size.

The input beam may be uncollimated, in which case the optical elements of the system will have slightly different powers so as to ensure that the output beam is collimated.

In view of the Fresnel diffraction fringing or ringing which tends to develop at the edge of a beam propagating away from an aperture or the edge of a stop portion, it is preferred to use a further optical system such as a telescope so that an image of the stop is focussed on the surface to be eroded. In this manner, a sharp edge can be provided for the beam at the surface and an even illumination within the beam.

Since the shape of the beam delivered to the surface will correspond to the shape of the aperture in the stop, a wide range of beam shapes is available.

If it is desired to increase the curvature of a surface, the opposite (ie convex erosion) profile must be used. To this end a concave conical lens, or other beamsplitting device, may be utilised to create an annular region of illumination with a central region having zero or minimal illumination.

By using a complementary convex conical lens in combination with a concave conical lens, the diameter of the illuminated annulus can be adjusted by altering the axial distance between the convex conical lens and the concave conical lens.

Alternatively, mirrors may be used. A mirror having an elliptical aperture may be located at 45 degrees to the illumination axis of the laser and positioned relative to the surface which is to be irradiated so that the image of the hole in the center of the mirror is coincident with the center of the region of the surface which is to be exposed. The size of the illuminated annulus can be altered by changing the mirror. A mirror is especially useful for providing a variable width non-illuminated strip. Two mirror portions may be provided separated by a gap which results in the non-illuminated strip. By moving the mirror portions towards and away from each other, the width of the strip can be varied.

The system described above, using a stop movable along the axis of the beam, may also be used to provide a beam with a central non-illuminated strip or spot. This is accomplished by providing a shaped central stop portion, either alone or in an aperture in a larger stop.

Since the normal surface of a cornea is convex, the result of forming a concave profile effectively will flatten the surface of the cornea slightly.

Flattening the surface of the cornea serves to decrease the refractive power of the eye.

Conversely increasing the curvature of the cornea (by effecting a convex erosion), increases the refractive power of the eye.

Where the erosion is to be effective parallel to a line rather than around a point, cylindrical lenses or plain mirrors or slits may be used to produce rectangular regions of illumination of variable width. Such techniques can be employed on a cornea to correct astigmatism and suchlike.

According to a preferred feature of the invention, a more uniformly eroded surface is achieved by inducing a gaseous flow over the surface during the erosion process to remove debris arising from the interaction of the laser beam with the surface.

Where the surface which is to be eroded is the cornea of an eye, the gas is conveniently Nitrogen.

Where the invention is to be used for corneal reprofiling, a surgical microscope may be employed to allow the surgeon to aim the laser correctly.

For example, in one possible method, a laser system capable of measurement and reprofiling is incorporated in an apparatus which includes a suction cup for stabilising the eyeball relative to the system. After initial setting up and alignment using the measurement mode, reprofiling is effected by appropriate operative signals from the control unit using the reprofiling mode, with remeasurement between either each reprofiling step or after a sequence of steps in order to check progress towards the intended final profile. This is essential because both the eye chemistry and the conditions of use of the apparatus can vary sufficiently to affect the amount of reprofiling effected with a given dosage of laser energy.

It is possible to monitor and/or at least in part control the operation using a computer which at the start is input with the final corneal shape required, is input during the operation with shaping measurements from the measurement mode of the laser which indicates progress, and outputs controlling signals to the laser accordingly.

The wavelength of a laser used for corneal reprofiling is important. Typically the wavelength may be about 193 nm, although both shorter wavelengths down to 157 nm (for a Fluorine laser) and longer wavelengths up to 15 um may be employed. However, but the sub-range 300 nm to 1400 nm should not be used as it is dangerous to underlying tissues of the eye. It is important, with respect mainly to the wavelength in question, that the laser energy should not penetrate the eye, since the cells lying below the collagen layer are easily damaged.

Since reprofiling requires use of a laser beam of changing cross-sectional area, it is preferred to supply the energy through a UV optical system which produces a beam having constant energy per unit area regardless of its varying cross-sectional size. A suitable UV optical system for this purpose is an optical stop with first and second zoom systems upstream and downstream thereof, the zoom systems being coupled for simultaneous adjustment. Alternatively, the system described above using a movable apertured stop may be used.

The apparatus may include a rigid frame attached to a headrest and a base unit within which a vacuum pump can be located.

BRIEF DESCRIPTION OF THE DRAWINGS

The invention will now be described by way of example with reference to the accompanying drawings, in which.

DETAILED DESCRIPTION OF THE DRAWINGS

Figure 1:
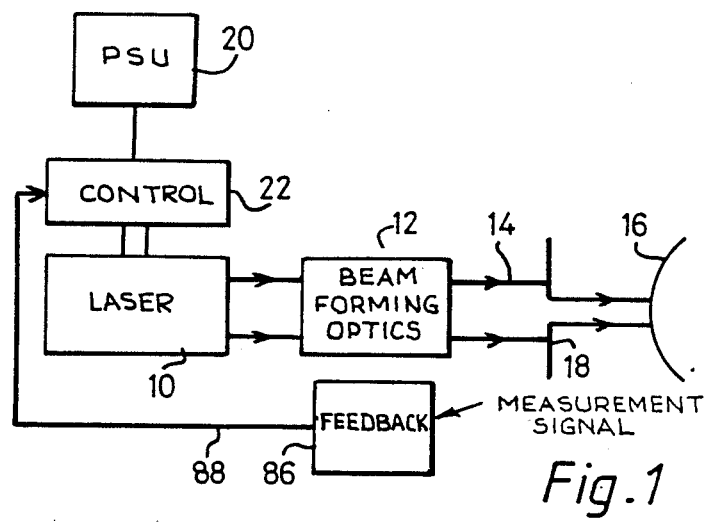
FIG. 1 is a diagrammatic illustration of apparatus for practising a method of reprofiling the surface of a convexly curved object, in accordance with the invention.

In FIG. 1 a laser 10 provides a light output to a beam forming optical system 12 which produces a relatively large diameter monochromatic beam of light 14 having a given wavelength. The beam is relayed to the object which is to be reprofiled and which as shown may comprise the cornea of an eye 16. Between the beam forming optical system 12 and the surface of an object 16 is located an aperture 18 or other beam dimension control means. The size of the aperture 18 determines the area of the object which will be illuminated.

The laser 10 is powered by a power supply unit 20 and a control circuit 22 which is adjustable to cause the laser 10 to produce pulses of light at a given frequency. Preferably the power is adjustable to control the energy of the pulses.

The aperture 18 may be fixed or variable.

Figure 2:
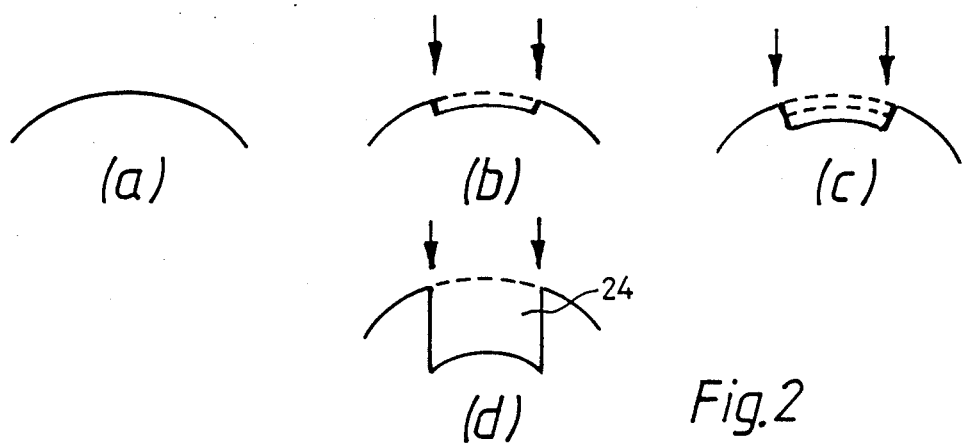
FIGS. 2a–d illustrate how ablation of the surface occurs with successive pulses.

In the case of a fixed aperture 18, the result of successive pulses of energy arriving at the surface of the object is shown in FIG. 2. The original surface is shown at FIG. 2A and at FIGS. 2B and 2C can be seen the same surface after one and then two pulses have been received.

After a large number of pulses have been received by the same area, a relatively deep recess 24 will be formed in the surface, the shape of which will be determined by the shape of the aperture 18, which will typically be circular. In this event, the recess 24 will be in the form of a generally circular hole in the surface.

Erosion of the form illustrated in FIG. 2 may for example be used in the preparation of the corneal bed for a corneal transplant operation.

If the beam used in FIG. 2 were cylindrical, or some other shape in which an illuminated region surrounds a region of reduced (or zero) illumination, erosion of the type illustrated in FIG. 2 could be used to prepare the implant (known as the "donor button") for a corneal transplant operation. In this case, the laser erosion would be continued until it cut completely through the donated cornea, and the button for the implant operation would be provided by the portion left by the region of reduced (or zero) illumination.

Figure 3:
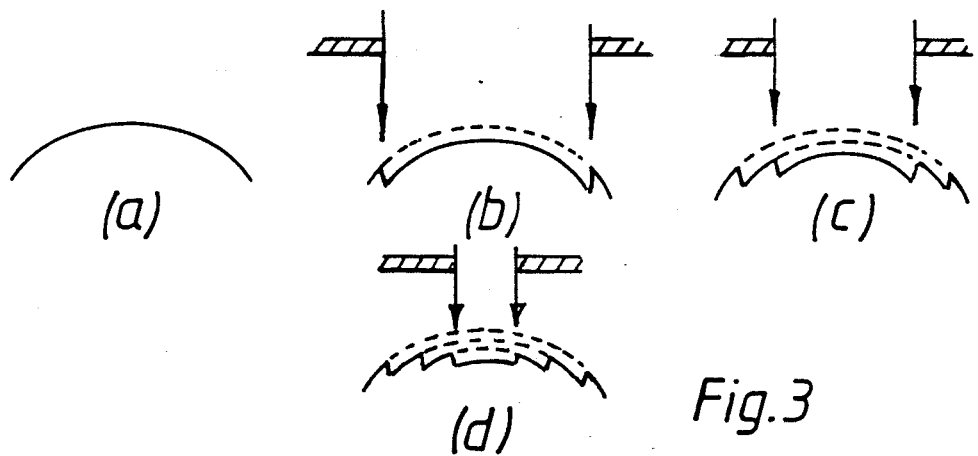
FIGS. 3a–d show how different profiles can be obtained by altering the size of the area over which the pulses are applied.

At present if, as is usual, the donor button is removed using a trphine, the corneal transplant has to be circular, as a trephine is only capable of cutting a circular section. However, if laser erosion is used, the shape of the donor button could be varied. This may be advantageous as the shape of the donor button can be used to determine the orientation in which the donor button fits into the prepared bed in the patient's cornea FIG. 3 illustrates how, by changing the aperture over a period of time during which pulses are continually supplied to the surface, a reprofiling of the surface is achieved. Thus, with a large aperture 18, a small amount of material will be removed from a relatively large area of the surface. If the aperture is then reduced before the other pulses are received, the resulting ablation caused by the following pulse(s) will be over a smaller area, and the profile will change to that of FIG. 3C.

If the aperture is then further reduced in size, the following pulse(s) will produce ablation over an even smaller area as in FIG. 3D etc. The result will be a general flattening of the surface relative to the original profile of FIG. 3A.

Figure 4:
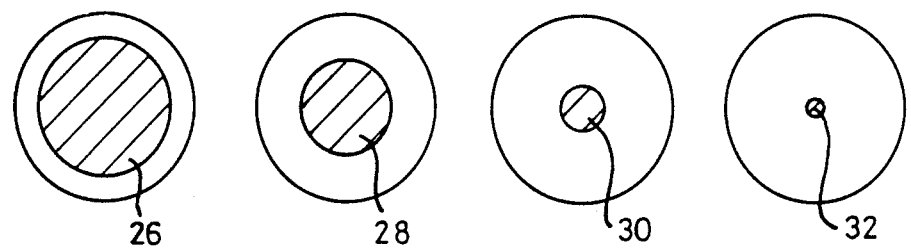
FIG. 4 illustrates diagrammatically the successive steps needed to reduce the curvature of a surface.

The illumination of the surface during successive pulses obtained by reducing the aperture 18 is shown in FIG. 4. Thus the area which has been illuminated by the laser is shown with a cross hatching at 26, 28, 30 and 32. In each case the aperture has been reduced considerably relative to its size during the delivery of the preceding pulse(s).

Figure 5:
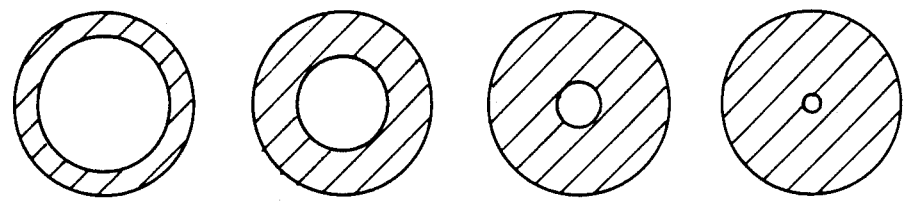
FIG. 5 illustrates diagrammatically the areas which must be exposed to pulses in successive steps so as to increase the curvature of the surface.

As illustrated in FIG. 5, a stop rather than an aperture is used, and a shadow of the stop is caused to appear on the surface, the area which is illuminated (again shown cross hatched) can be increased in size during successive pulses from a narrow annulus in the first instance to most of the circular area.

Figure 6:
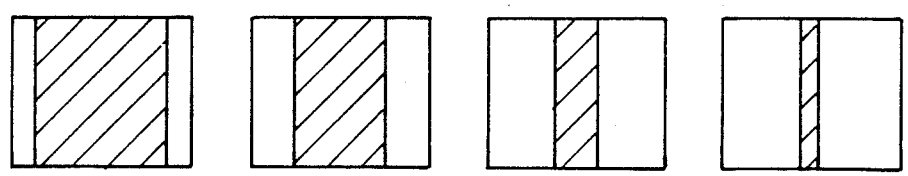
FIG. 6 illustrates cylindrical power correction so as to reduce the cylindrical curvature of the surface.
Figure 7:
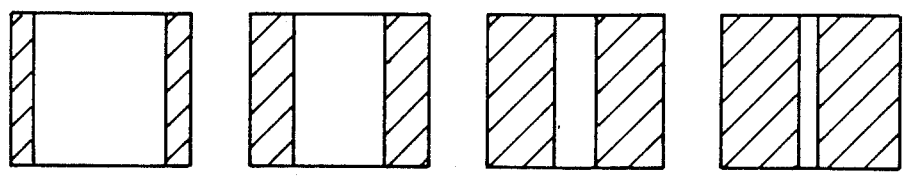
FIG. 7 shows the opposite arrangement which increases the cylindrical curvature of the surface.

If a nonsymmetrical aperture or stop is used (such as a slit or linear stop), the cylindrical curvature of the surface can be altered as shown in FIGS. 6 and 7 where, as in FIG. 4 and 5, the area illuminated by the laser is shown cross hatched.

The results of FIG. 6 can be obtained by using a slit of variable width and successively reducing the slit width so as to obtain narrower bands of illumination.

The results of FIG. 7 are achieved by using an opaque stop and varying the width of the stop so that more and more of the surface is illuminated.

It is to be understood that the object shown in the FIGS. 1 to 7 may be the cornea of an eye.

FIGS. 1 to 7 have illustrated in schematic form the manner in which a surface may be eroded and reprofiled by controlling and varying the shape and size of a laser beam. Although the different reprofiling regions have been discussed in terms of apertures and stops, there is a wide variety of beam-shaping optical systems that may be used as the beam dimension control means. Specific arrangements of possible beam dimensions control means will now be discussed.

Figure 8:
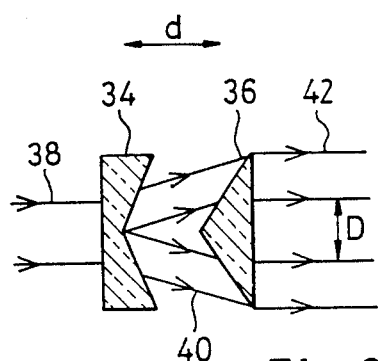
FIG. 8 illustrates diagrammatically how an illuminated annulus can be obtained and how the internal diameter of the annulus can be varied.
Figure 9:
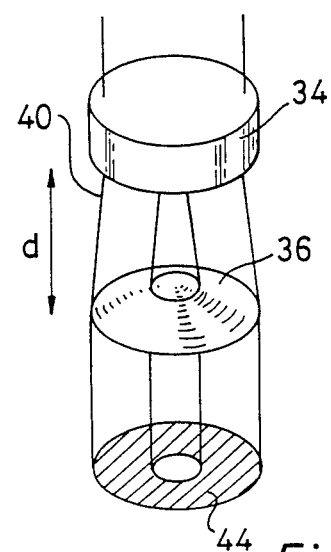
FIG. 9 is a perspective view of the elements shown in FIG. 8.

The apparatus of FIGS. 8 and 9 is usable to produce the illumination pattern of FIG. 5 by refraction. Here a plano-concave-conical element 34 is spaced by distance d from a complementary plano-convex-conical element 36. The two elements 34 and 36 will fit intimately together if moved into contact.

A parallel beam of light 38 incident on the plane surface of the element 34 is split at the conical surface into a diverging annulus of light 40 which is then refocussed by the element 36 into a cylindrical annulus 42. The diameter of the non-illuminated central region D is determined by the spacing d between the element 34 and the element 36.

FIG. 9 shows the elements of FIG. 8 in perspective and shows an illuminated annulus 44 formed on the surface of the object (not shown). The same reference numerals have been used in FIG. 9 as in FIG. 8 to indicate the different component parts of the system.

Figure 10:
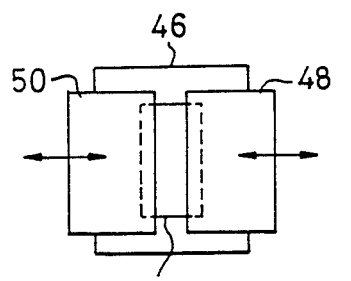
FIG. 10 illustrates diagrammatically a mechanism for producing a slit of adjustable width.

In FIG. 10 the component parts making up a slit of adjustable width are shown as comprising an apertured plate 46 having two movable plates 48 and 50 located in front thereof. The aperture in the plate 46 is denoted by reference numeral 52. As will be apparent movement of the plates 48 and 50 relative to the plate 46 produces changes in the width of the slit.

Figure 11:
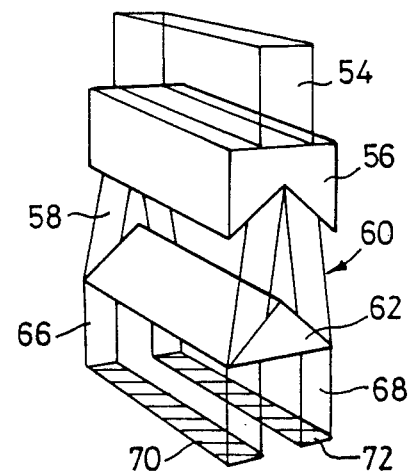
FIG. 11 illustrates a one dimensional version of the apparatus shown in FIG. 9.

FIG. 11 takes the refractive principle of the circular conical element systems of FIGS. 8 and 9 and adopts the same principle (albeit in one single dimension) to produce a pair of illuminated regions the distance between which can be varied simply by moving the one element further away from or nearer to the other. Thus, a parallel beam of light 54 incident on the plane surface of a concave prism 56 produces two diverging beams 58 and 60. A complementary convex prism 62 having inclined surfaces which complement the inclined faces of the concave prism 56, and a planar underside 64, is located downstream from the concave prism 56. Two parallel but spaced apart beams 66 and 68 emanate from the planar underside 64 in the same way as the ring of light emanates from the plane surface of the element 36 in FIG. 8.

By moving the concave prism 56 nearer to the convex prism 62, the two illuminated regions 70 and 72 move closer together and vice versa.

It should be noted that the systems of FIGS. 8, 9 and 11 use straight-sided-concave and straight-sided-convex elements (ie conical elements) rather than spherical lenses, and V-section prisms, rather than U-section prisms (ie cylindrical lenses). The refractive system of FIG. 11 varies the beam dimensions but does not substantially vary the beam energy density with variation in dimensions. In general, purely refractive systems are suitable for creating a variable-size unilluminated gap in a beam, but are less suitable for producing a variable-size illuminated spot owing to the difficulty in varying the spot size by refraction while retaining constant beam energy density.

Figure 12:
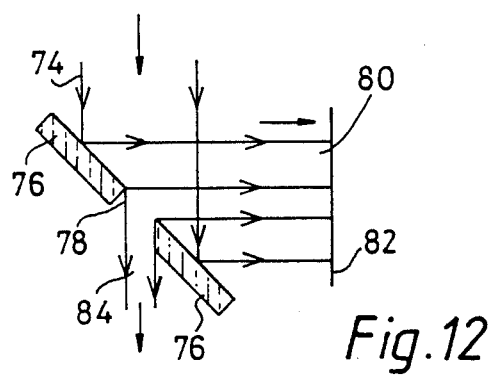
FIG. 12 shows how a 45 degree mirror arrangement can be used to produce the inverse of the adjustable slit of FIG. 10.

FIG. 12 illustrates a reflective arrangement in which a circular beam 74 incident on a mirror 76 having therein an elliptical hole 78 (circular as projected into the plane transverse to the beam), can produce a cylindrical beam 80 which will produce an annulus of illumination on a surface as 82. Light incident at the elliptical hole 78 passes through it as at 84. By substituting for the mirror 76 a further mirror having an elliptical hole of a different size, the size of the non-illuminated region of the surface 82 can be varied.

A one-dimensional system can also be produced in which the mirror 76 is replaced by two rectangular mirrors which can be moved closer together or further apart so as to define a slit of variable width, thus producing two parallel illuminated regions on the surface 82 which can be moved nearer together or further apart depending on the relative positions of the two mirrors. Light incident at the gap between the two mirrors will pass therethrough as in the case of a centrally apertured mirror. FIG. 12 can also be considered as illustrating this arrangement, if the two mirror portions 76 in the Figure are taken as the two rectangular mirrors.

A system including mirrors such as in FIG. 12 is particularly advantageous in that an alternative light source can be used to illuminate the surface 82 through the aperture 78. The illuminated region can's he viewed using a semi-reflecting mirror located within the optical path of the beam 74. In this fashion the operator can adjust the position of the mirror and optical system and/or the surface 82 so as to obtain just the desired alignment and positioning of the beam to produce the desired erosion of the surface by the pulses of laser energy.

As has already been indicated, it is preferable to effect reprofiling with a laser beam of constant energy per unit area, even though the cross-sectional area of the beam is varied as aforesaid. An arrangement for achieving this effect is shown diagrammatically in FIG. 13, which indicates a composite zoom system comprising zoom lens 90, a stop 92, and a zoom lens 94, and two zoom lenses 90, 94 being coupled at 96 for simultaneous adjustment. The zoom lenses are preferably afocal.

Because the two zoom lenses 90, 94 are coupled for simultaneous adjustment, adjustment of the zoom lens system does not affect the energy density of the laser beam output from the second zoom lens 94. However, as the position of the second 300 m lens 94 varies, the magnification of the stop in the output beam varies. Adjustment of the first zoom lens 90 does not affect the output beam size, but it is necessary to maintain the constant energy density of the beam.

Figure 14:
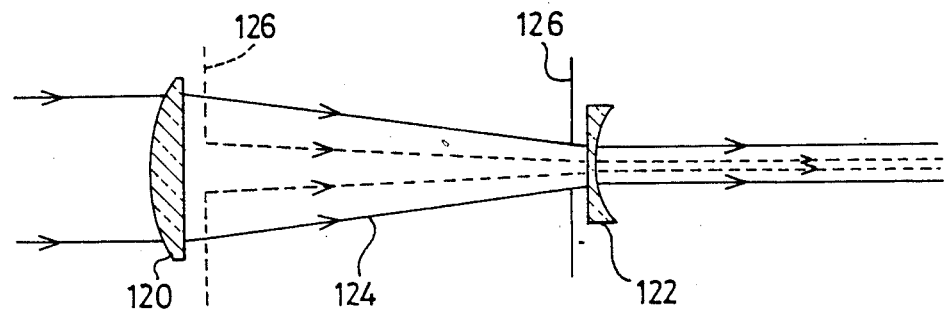
FIG. 14 shows a further arrangement for producing a variable size spot of constant energy density.

An especially preferred embodiment for the beam dimension control means is illustrated in FIG. 14. In this arrangement, two beam shaping elements such as a plano-convex lens 120 and a plano-concave lens 122 define an optical system which can receive as input, a collimated parallel laser beam of a first diameter and which can output a collimated parallel beam of a second diameter, with a converging (or alternatively diverging) beam portion 124 between them.

A stop 126 having a beam-shaping window or aperture (or a beam-shaping stop portion), is movable along the beam axis over the converging beam portion 124. In order to vary the size of the output laser beam, the aperture (or the stop portion in the stop 126) remains constant, but the stop 120 is moved axially along the beam between the two lenses 120, 122. The following description of the manner of operation of this arrangement is in terms of a stop 126 having an aperture to define the beam outer perimeter. However, a stop 126 having a stop portion to define a variable size region of reduced (or zero) illumination in the beam, would function in a corresponding manner.

When the stop 126 is adjacent the plano-concave lens 122, the plane of the stop 126 intersects the converging beam portion 124 at its smallest diameter. Thus all, (or a relatively large portion) of the beam, passes through the aperture in the stop 126. The edges of the laser beam in this case are shown as continuous lines in FIG. 14, as is this position of the stop 126.

However, if the stop 126 is moved so as to be adjacent the plano-convex lens 120, as shown in broken outline in FIG. 14, the plane of the stop 126 now intersects the convergent beam portion 126 at its greatest diameter. In this position, only a relatively small portion of the laser beam passes through the aperture in the stop 126, as the remainder of the beam strikes the stop 126 and is absorbed or deflected. Thus, in this case, the diameter of the beam downstream of the stop 126 is narrowed as also shown in broken outline in FIG. 14.

It will be evident that the central position of the beam, which passes through the aperture in the stop 126 in all cases, is not affected by the position or the presence of the stop 126. Thus it can be seen that the stop 126 does not affect the energy density of the final beam.

Accordingly, the size of the output laser beam can be varied simply by moving the stop 126 axially along the beam path. Since the stop 126 has no effect on the energy density of the beam (or portion thereof) passing through the aperture, so the energy density of the output beam remains constant while its size is varied. The shape of the output beam will of course be determined by the shape of the aperture in the stop 126.

Although in FIG. 14 the beam has been shown as converging between the two lens elements 120, 122, it will be readily apparent that the arrangement would work equally well if the concave lens element was upstream of the convex element so that the beam diverged between the two elements.

The arrangement of FIG. 14 imposes a constant overall alteration in the energy density and maximum width of the laser beam. In some circumstances, this alteration may be desirable or may be compensated for in beam-forming optics upstream of the arrangement shown. However, it may be convenient to provide a beam dimension control means which has no overall effect on the beam energy density and the maximum size. In this case, an arrangement may be used such as that shown in FIG. 15, in which a collimated parallel sided beam is first caused to diverge and then caused to converge again. The movable aperture 126 may be placed in either the divergent beam portion 128 or the convergent beam portion 130.

Figure 16:
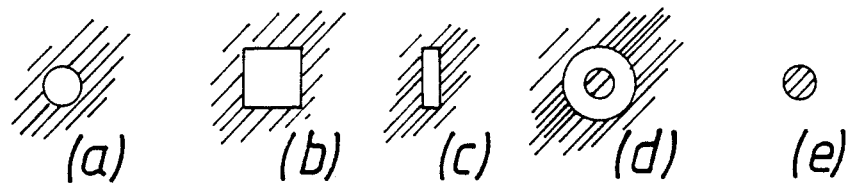
FIGS. 16a–e shows four alternative aperture shapes for use in the arrangement of FIG. 14.

FIG. 16 illustrates some possible shapes for the aperture and the stop portion of the stop 126. The apertures are shown as clear portions surrounded by shaded portions representing part of the material of the stop 126. As can be seen in FIG. 16(d), the stop 126 may have an aperture and a stop portion within the aperture.

The shapes shown in FIGS. 16 (a) and (b) may be used to prepare the bed for a corneal transplant. The shape shown in FIG. 16 (a) may also be used in reprofiling the cornea to reduce its curvature. The shape shown in FIG. 16 (c) may be used in reprofiling the cornea to correct astigmatism. The shapes shown in FIG. 16 (d) and (e) may be used to cut out the donor button for a corneal transplant and may also be used in reprofiling the cornea to increase its curvature.

The aperture in the stop 126 may be an optical aperture but not necessarily a physical aperture. That is to say, the aperture may be formed by a piece of highly transparent material. Thus, the stop 126 may be formed of a transparent body onto which is placed an opaque layer having the desired shape. Such a construction makes it relatively easy to provide aperture shapes and stop portions such are shown in FIG. 16(d) and 16(e,) in which an unobscured portion entirely surrounds a central obscured portion.

Figure 13:
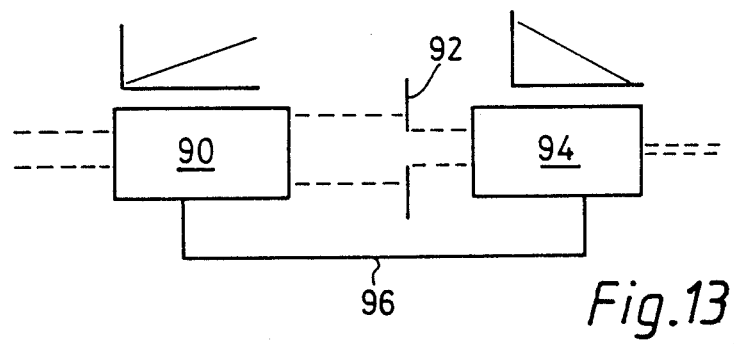
FIG. 13 shows an arrangement for producing a variable size spot of constant energy density.

In theory, the arrangements shown in FIGS. 13 and 14 could in many instances be replaced by a variable-size iris diaphragm. However, the range of shapes which can be defined by an iris diaphragm is limited, and furthermore the shape of the aperture defined by an iris diaphragm does not normally remain precisely constant as the diaphragm is closed down or opened up. Thus, for precise work an arrangement is preferred where variations in the apparent size of an aperture in a fixed stop is employed such as in FIGS. 13 and 14.

Figure 17:
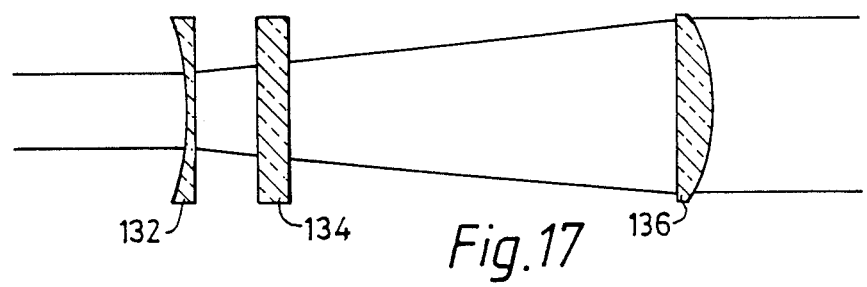
FIG. 17 is a sectional view of a beam forming optical system.
Figure 18:
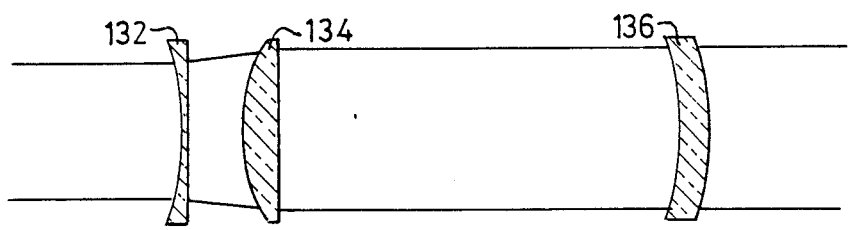
FIG. 18 is a sectional view of the optical system of FIG. 17 seen in a direction transverse to the direction of the view of FIG. 17.
Figure 19:
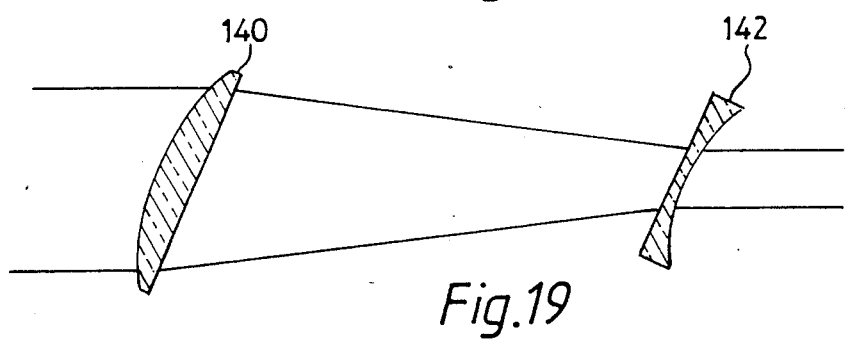
FIG. 19 is a sectional view of an alternative beam forming optical system.

The beam forming optical system 12, shown in FIG. 1, may not always be necessary, should the laser output beam be directly usable. However, with most lasers it will normally be desirable to perform some initial beam-forming operations typically to change the shape of the beam. Thus, some types of laser typically produce a beam of rectangular or elliptical section, (for example, the Excimer lasers typically produce rectangular section beams) and it will normally be preferable to provide to the beam dimension control means, a beam having a square or circular cross-section. FIGS. 17 to 19 show embodiments of beam forming optical systems.

The arrangement of FIGS. 17 and 18 uses cylindrical-surfaced lens elements as well as spherical surfaced lens elements. The two Figures are section views of the same elements but viewed in orthogonal directions, so that FIG. 17 can be regarded as a sectional side view while FIG. 18 can be regarded as a sectional stop view.

A parallel sided laser beam having a cross-section of unequal axes is delivered to a plano-spherical concave element 132, which causes the beam to diverge. The 's beam then strikes a nearby plano-cylindrical convex element 134. The cylindrical axis of the planar-cylindrical convex element 134 is in the direction of the shorter beam cross-section axis, so that it the plano-cylindrical convex element 134 has no converging effect on that axis of the beam, and the shorter axis of the beam continues to increase as the beam leaves the element 134. However, its cylindrical convexity causes the element 134 to deflect the edges of the beam at either end of the longer axis of the cross-section of the beam.

On leaving the element 134 the beam continues to diverge in one direction, increasing the length of the shorter axis, while remaining constant in the transverse direction, so that the longer axis of the beam remains unchanged. A further optical element 136 is spaced downstream of the beam from the plano-cylindrical convex element 134. This further element 136 is cylindrical-concave on its upstream face and spherical-convex on its downstream face and its cylindrical axis is parallel to the cylindrical axis of the element 134, so that it serves to converge the beam at opposite ends of its (hitherto) shorter axis, whilst having no effect on the length of the (hitherto) longer axis of the beam.

The effect of the arrangement shown in FIGS. 17 and 18 is that, following the divergence of the beam caused by the element 132, the shorter axis of the beam cross-section continues to increase until the beam reaches the element 136, whereas the longer axis of the beam cross-section increases only until it reaches the element 134. In this way, the shorter axis is increased by a greater amount than the longer axis, and the beam output from the element 136 has equal cross-sectional axes.

It should be noted that the unequal treatment of the cross-sectional axes of the beam, whereby one axis is expanded by a greater extent than the other, does not introduce non-uniformity of energy density if the beam previously had uniform energy density at all point on its cross-section.

FIG. 19 shows an alternative arrangement in which a beam having unequal cross-sectional axes may be converted to a beam having equal cross-sectional axes. This system comprises a plano-convex element 140 and a plano-concave element 142. The curved surfaces of both of these elements are spherical. However, they are both aligned with their planar surfaces oblique to the axis of the laser beam, so as to have a greater effect on one axis of the beam cross-section than on the other.

Figure 20:
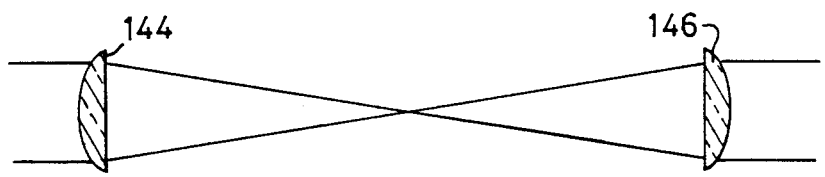
FIG. 20, is a sectional view of a relay telescope.

An optical system for delivering a laser beam to a surface to be eroded may comprise merely the beam forming optics of FIGS. 17 and 18 (or FIG. 19), followed by a beam dimension control means such as shown in FIG. 13 or FIG. 14. However, where the beam has to travel relatively long distances between optical components or between an optical component and the surface to be eroded, a relay telescope is preferably provided as shown in FIG. 20. Such a telescope can be very simple and may be made solely of two converging lenses 144, 146. These telescopes are particularly useful if they are arranged to image the output of the upstream optical component onto the input of the downstream component or onto the surface to be eroded.

It is especially advantageous to provide between the beam dimension control means and the surface to the eroded, a relay telescope which focusses onto the surface to be eroded an image of the aperture which defines the beam shape. This assists in providing uniform illumination over the irradiated area and provides a sharp edge to the irradiated area. In the absence of such a re-imaging of the aperture, the theoretically obtained beam shape would be degraded at the surface to be eroded by the effect of Fresnel diffraction fringing or ringing which tends to develop at the edge of the patch as the beam propagates away from the aperture. By focussing an image of the apertue, all light propagating from a single spot of the aperture is focussed to a single spot on the image, thereby eliminating the diffraction fringing or ringing.

Figure 21:
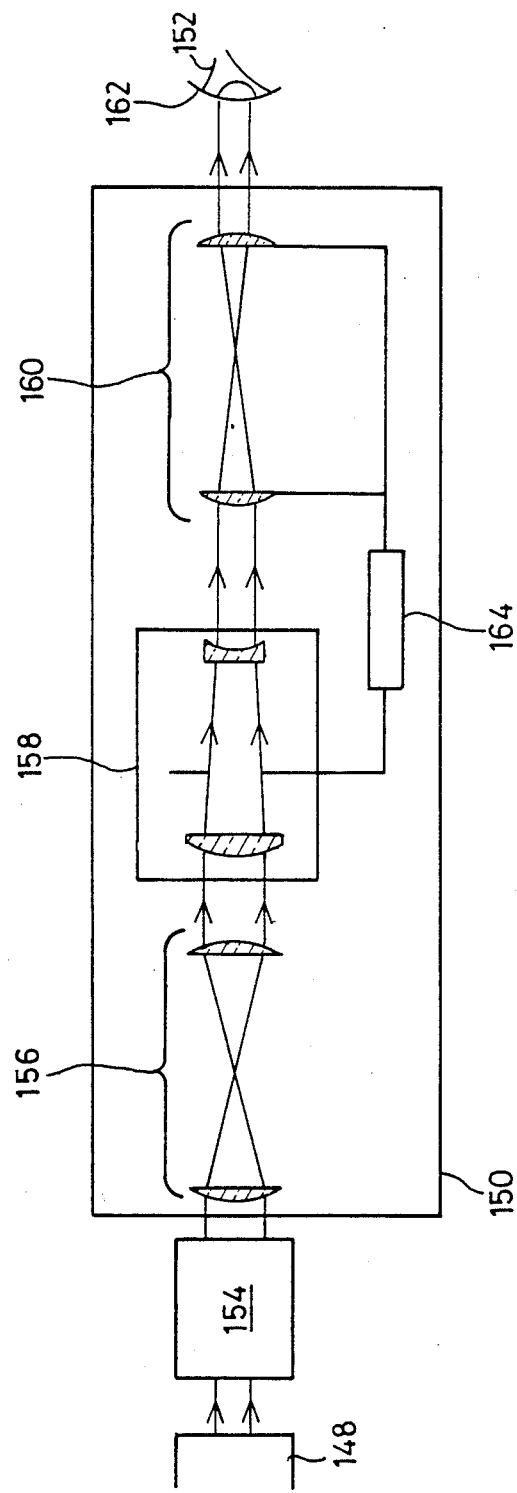
FIG. 21 is a schematic view of the optical system from the laser to the cornea of the eye.

Accordingly, a preferred optical delivery system, for producing from a laser a for eroding the cornea of the eye, is shown in FIG. 21. In this Figure, the light from a laser 148 passes through a beam forming optical system 154 and then enters an articulated arm 150 which houses the remainder of the optical system and delivers a beam of the desired shape and size to the cornea of an eye 152.

The beam forming optical system 154 is equivalent to the optical system 12 in the schematic arrangement of FIG. 1. Typically it will comprise an arrangement such as is shown in FIGS. 17 and 18 or as shown in FIG. 19.

From the beam forming optical system 154, the beam enters a first relay telescope 156. This delivers the beam to a beam dimension control means 158. As shown, the latter is a system as shown in FIG. 14. However, various other arrangements such as are described with reference to FIGS. 8 to 13 could be substituted for the system shown.

From the beam dimension control means 158 a second relay telescope 160 delivers the beam to the corneal surface 162 of the eye 152.

Figure 15:
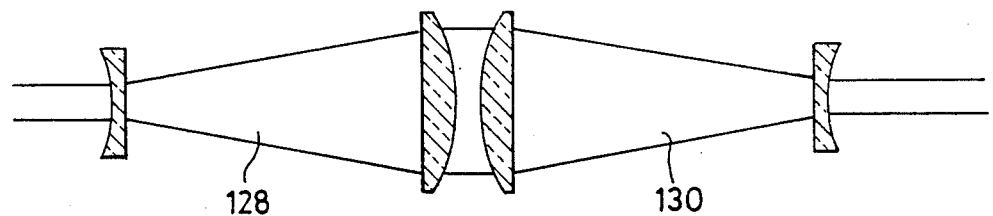
FIG. 15 shows an arrangement incorporating the arrangement of FIG. 14 but having no overall effect on the energy density of the beam.

Since the apertured stop 126 is moved axially along the beam in order to vary the size of the illuminated area on the corneal surface 162, the second relay telescope 160 will not always provide a precisely focused image of the aperture in the stop 126 if the telescope 160 has a fixed focal length. Accordingly, it may be desirable to provide a gearing connection 164 between the elements of the second relay telescope 160 and the apertured stop 126 when an arrangement such as that shown in FIG. 15 is used as the beam dimension control means 158. This ensures that movement of the apertured stop 126 is accompanied by the appropriate corresponding movement in the elements of the second relay telescope 160 to maintain an in-focus image on the corneal surface 162. On the other hand, the second relay telescope 160 receives the image of the apertured stop 126 through the plano-concave lens 122, and this has the effect that the apparent location of the apertured stop 126 to the second relay telescope 160 (ie, the location of the virtual image created by the lens element 122) moves axially much less than the actual axial movement of the stop 126. Consequently, it may not be necessary to provide for automatic adjustment of the second relay telescope 160 with movement of the stop 126.

As mentioned above, the arm 150 which houses the optical system is articulated.

Although the invention has been described as being particularly applicable to reprofiling the surface of the cornea of the eye, it will be seen that the invention is of equal application to the profiling of the surface of any object capable of being ablated by the laser beam. Thus, the invention may be used to profile the surface of a lens or mirror or may be used to form precisely shaped windows in surface coatings on objects which are either curved or flat.

Figure 22:
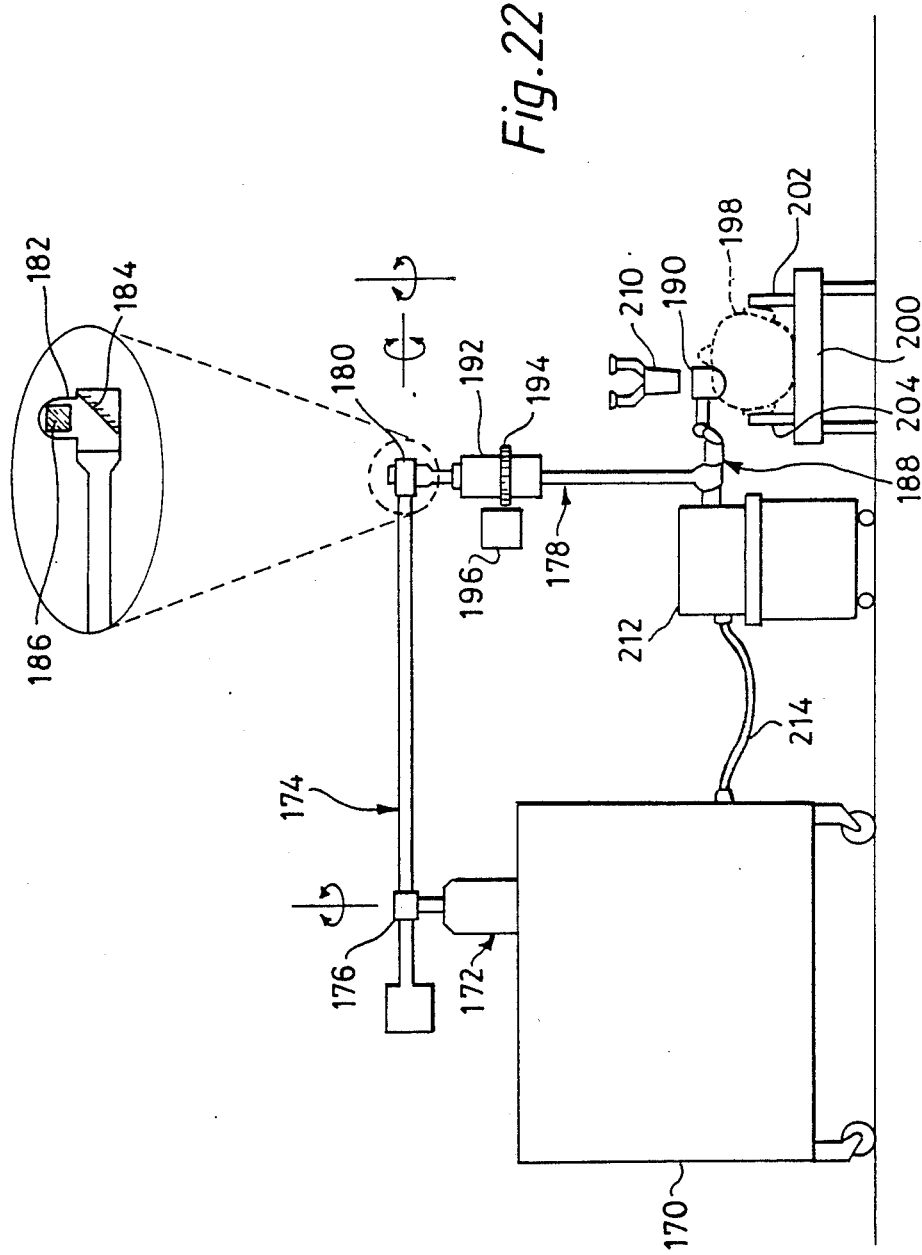
FIG. 22 shows a laser apparatus for measurement and reprofiling.

FIG. 22 illustrates apparatus for performing a method of the present invention for the reprofiling the cornea of the human eye or the erosion of ulcers therefrom. A laser and associated control circuitry is contained in a housing 170. The beam forming optics, for providing a beam of a desired standard shape and size before entering the beam shaping optics, is also contained within the housing 170 together with the laser power supply and control circuits.

It is important to provide a beam of substantially uniform intensity across the beam cross-section. The output of an Excimer laser is substantially uniform across a first cross-sectional axis, but across the second cross-sectional axis transverse to the first there is a slight falling off of intensity at the edges of the beam. Therefore an aperture is placed at the laser output to mask off the non-uniform edges of the beam and the beam delivered to the mask forming optics has a substantially uniform cross-section.

The laser beam leaves the housing 170 in a vertical direction, and enters support 172 for an articulated arm.

The first section 174 of the arm pivots about the support 172 through a joint only having one degree of freedom. A second arm portion extends orthogonally the first section 174 to which it is joined by a joint 180 having two degrees of freedom.

The joint 176 includes a single plane mirror (not shown) for reflecting light from within 172 along 174.

The inset in FIG. 22 shows part of the joint 180 from above. The two arm sections 174 and 178 are joined by a coupling 182 which is arranged to rotate with respect to each arm portion about the axis thereof. Two fixed plane mirrors (184, 186) are arranged in the coupling 182 to reflect light parallel to the axis of the first arm section 174 along the axis of the second arm section 178, regardless of the angular position of the coupling 182 relative to the arm portions. For this to function it is important that the axis of rotation of each arm passes through a central region of its respective mirror, the mirrors 184, 186 being positioned relative to one another so that light incident on one along the axis of the respective arm portion is reflected to the other mirror to be reflected along the axis of the arm portion. In a similar manner a knuckle joint 188 having 3 degrees of freedom has three plane mirrors to enable light to pass from arm portion 178 through the knuckle to an eyepiece 190.

The first arm portion 174 contains the first relay telescope 156 of FIG. 21.

The second arm portion contains the beam dimension control means 158 and the second relay telescope 160 of FIG. 21.

The beam dimension control means 158 is housed in a widened section of the arm 192 having a knurled ring 194, rotation of which operates the beam dimension control means 158 to vary the beam dimensions. The knurled ring 194 may be driven by a motor 196 so that it may be remotely and/or automatically operated The articulation joints of the arm and the terminating knuckle enable the eyepiece 190 to be manouvered easily into the correct position and orientated relative to the eye of a patient whose head is shown at 198.

As shown in FIG. 22 the patient is lying face upwards on an operating table 200. The operating table 200 will supports the patient's head against vertical movement If desired, side-supports 202, 204 may be provided to restrain sideways movement of the head.

The articulated arm assembly 174, 178 is conveniently a modification of a standard laser arm obtainable from Laser Mechanisms of Bloomfield Hill, Mich. USA. This arm must be modified to incorporate the beam dimension control means and the relay telescopes, and it may also be necessary to replace some of the mirrors provided at the joints in the arm. However, by using either the original mirrors or further mirrors mounted on the original mirror mountings, it is possible to ensure that reflections at the joints in the arm do not alter the beam optics provided by the elements illustrated in FIG. 21.

In use, the apparatus would be used in conjunction with a Nitrogen gas supply to be applied to the patient's eye and a suction means for providing suction to clamp the eyepiece over the patient's eye. These are both located in the housing 170. The Nitrogen may also be used to purge the arm of gases opaque to the laser wavelength in the case of an ArF laser. The arm may also be used to deliver the Nitrogen to the eye.

Figure 23:
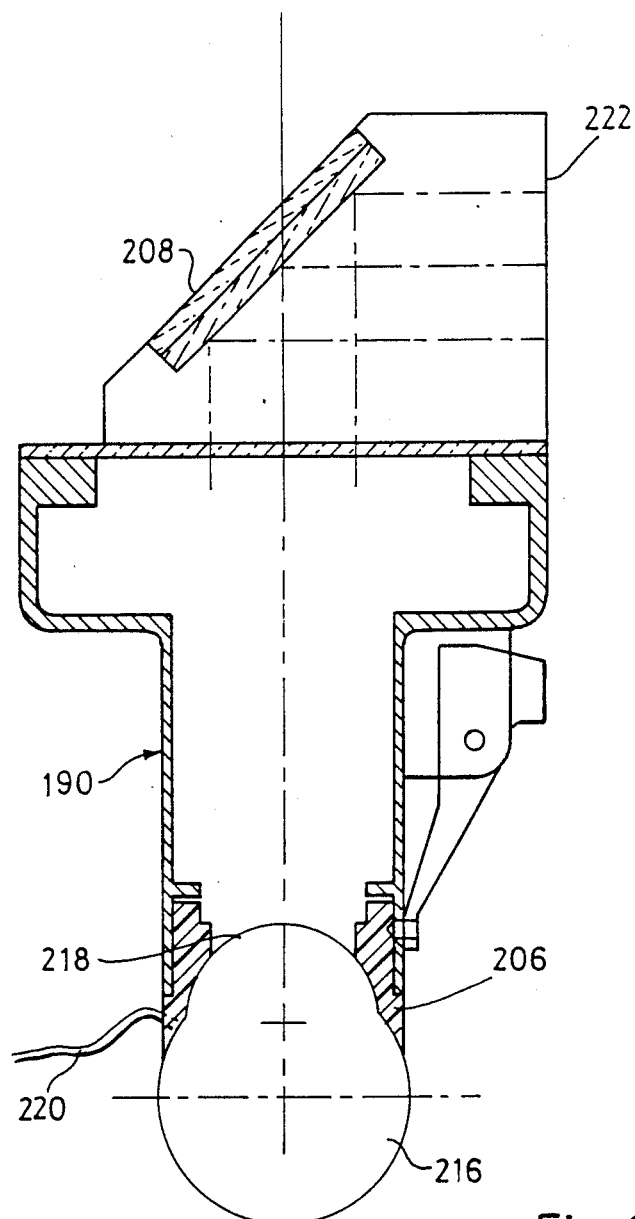
FIG. 23 shows an arrangement of a suction cup on an eye and the downstream end of an optical system connected to it.

The eyepiece is shown to an enlarged scale in FIG. 23 and includes a cup 206, of resiliently deformable flexible material such as rubber or plastics, which when placed over the eyeball will clamp thereto on being evacuated.

The eyepiece 190 includes a window having a semi-reflecting mirror 208 through which the eye can be observed using a surgical microscope 210 which latter is supported thereabove by any convenient means. The surgical microscope 240 may be connected to the eyepiece 190, but will more normally be separate therefrom and supported by an arm (not shown) from the ceiling or by a cantilever (not shown).

A further mirror (not shown), possibly in the knuckle 188, allows the simultaneous connection of an automatic measuring device 212 such as a profilometer or keratometer. The output of the measuring device 212 may be connected via a line 214 to a computer (not shown) which is adjusted to control the operation of the laser so as to obtain the desired corneal shape.

Thus the desired corneal shape may be input initially to the computer and the corneal shape measurements provided to the computer during the operation can be used to indicate the progress towards the desired final shape so that the computer can output control signals to the laser system accordingly. Preferably, the computer is microprocessor based and may be located at least in part within the housing 170.

The wavelength of the radiation of the reprofiling laser is important, and typically is of the order of 193 nm, although shorter wavelengths down to 157 nm (for a fluorine laser) or longer wavelengths up to 15 um may be employed. It is important, with respect mainly to the wavelength in question, that sufficient laser energy should not penetrate beyond the cornea to cause damage to the cellular tissue. Therefore the sub-range 300 nm to 1400 nm should be avoided as the underlying cellular tissue of the eye is easily damaged by these wavelengths.

Referring again to FIG. 23 the suction cup 206 fits over the sclera of the eye 216, leaving the corneal surface 218 unobstructed. A flexible tube 220 supplies vacuum suction to the cup, so as to clamp it to the eye with a force sufficient to hold it in place but not to distort the shape of the cornea.

As shown in FIG. 23 the mirror 208 enables the optical system of the laser to extend laterally from the patient, the knuckle 188 being secured to the end face 222 of the eyepiece housing.

As an alternative, the mirror 208 may be omitted and the optical system can extend straight ahead from the patient.

As a further alternative, a mirror unit (not shown) similar to that shown in FIG. 23 may be used, but which has a semi-reflecting or wavelength selective mirror enabling two optical systems to be connected thereto both of which are aligned with the corneal surface 218. This arrangement allows the optical system from the laser to be connected in addition to a microscope or other observation device for use by the operator or an automatic keratometer.

In a first method of using the apparatus of FIGS. 22 and 23 no automatic feedback control is present and the line 214 is not required. The measuring device 212 in this method is a commercially available keratometer such as the "Photokeratoscope" or the "Corneascope" referred to above, which may be operated in the manner described in the article by S. D. Klyce referred to above. These devices work by imaging patterns, usually concentric rings, on the corneal surface. Preferably the keratometer used in the present method is modified slightly to increase the number of lines imaged on the central portion of the cornea and thus increase the amount of information available about the curvature of the central portion.

In this method, the keratometer 212 may be connected to the knuckle 188 as shown, or may be movable when needed to occupy the position shown for the surgical microscope 210 the operator moving the keratometer 212 or the microscope 210 into the position as required.

The suction cup 206 will normally be is attached to the patient's eye 216, first and thereafter the eyepiece housing 190 fitted thereto. The nitrogen supply is then turned on. The keratometer 212 is used to check that the suction cup has not affected the corneal profile. Preferably a visual inspection of the eye is also made using the microscope 210. Then the beam dimension control means is operated via the knurled ring 194 to select the desired area of irradiation by the beam on the cornea.

The laser is then turned on, preferably set to operate at a relatively slow pulse rate such as 5 Hz.

After a predetermined period, normally 30 seconds or less, the laser is turned off, the beam dimension control means 158 adjusted so as to define a different area for irradiation, and the laser turned on again. This process is repeated so as to provide a series of exposures of predetermined areas of the cornea to be predetermined numbers of pulses. As will be evident, the choice of size and shape of the areas and the numbers of pulses determines the nature of the reprofiling performed on the cornea.

The parameters are selected to produce 75% of the desired final correction to the corneal profile. The cornea is then measured again using the keratometer 212, and the exact correction remaining to be made is determined. The laser apparatus is then operated again in a similar manner to that just described, with the parameters selected to produce 75% of the correction remaining to be made. The process is then repeated until the correction remaining to be made is considered to lie within acceptable limits.

This continuous approximation process is relatively slow, and puts demands on the operator, but has the advantage that no feedback control circuits are necessary to control the laser.

It will be seen that if a constant frequency pulse rate is employed, the number of pulses per exposure will be proportional to time, and it is then sufficient to merely measure the duration of each exposure to ensure a predetermined number of pulses are received by the cornea.

In a variation of this method, the knurled ring 194 of the beam dimension control means 158 is motorised and both the motor 196 and the laser are under the control of a microprocessor located in the housing 170. In this case, the microprocessor can implement the procedure of turning the laser on and off and adjusting the beam dimension control means 158. More preferably, the laser is pulsed continuously while the microprocessor adjusts the beam dimension control means 158 to follow a predetermined time/beam dimension curve. This may involve periods in which the beam dimensions are adjusted continuously while the laser is pulsed. The continuous adjustment of the beam dimensions means that the boundary between regions which are and are not being irradiated travels relatively smoothly over the surface of the cornea, giving a relatively smooth reprofiling to the surface.

The time/beam dimension curve is selected, relative to the pulse rate and beam wavelength and intensity of the laser, to produce 75% of the desired final correction as referred to above.

Strict control of the laser is required. To this end these may be provided a feedback device 86 as shown in FIG. 1, which receives information from optical or other inspection of the surface which is being exposed to bombardment of the pulses of laser energy. A feedback path 88 communicates with the control circuit 22 for controlling the laser 10. Thus, for example, the actual duration and amplitude of the pulses supplied by the laser may be tuned so as to produce just the desired degree of erosion of the surface by each pulse. In the event of excessive erosion, subsequent pulses can be either substantially reduced in size or inhibited. Conveniently an alarm system (not shown may be provided in conjunction with the feedback device 86 to inhibit further operation of the device and indicate an error condition in the event that unexpected erosion of the profile occurs.

Figure 24:
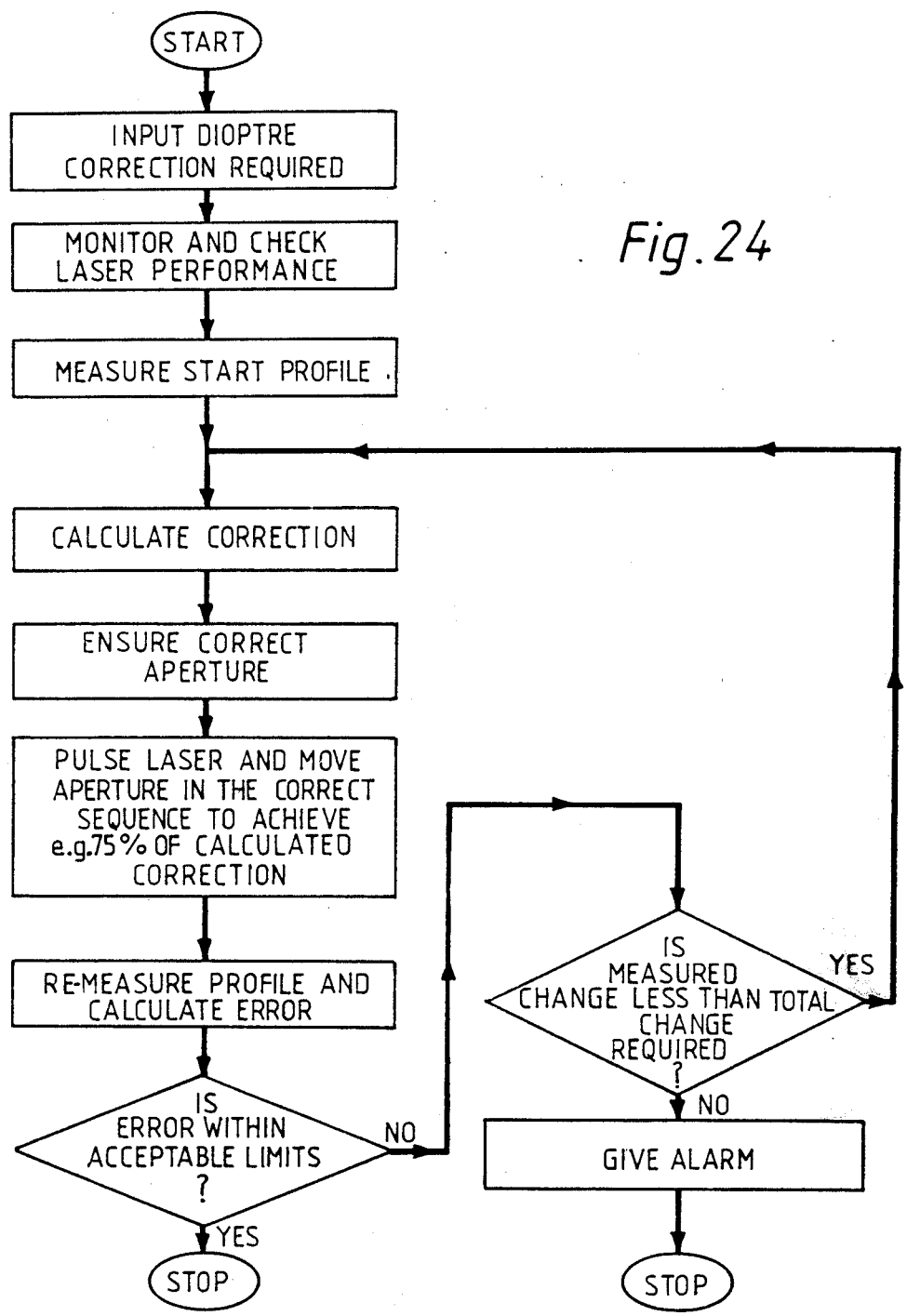
FIG. 24 is a flow diagram of the operation of feedback control circuits.

FIG. 24 is a flow diagram of the operation of the control circuit 22 during a feedback control operation. The control circuit 22 is preferably provided at least in part by a microprocessor or microcomputer.

In a second method of using the apparatus of FIGS. 22 and 23, feedback control of the laser and its optical system is provided. The keratometer 212 is connected as shown in FIG. 22 and the line 214 is connected and used to supply the output of the keratometer 212 to a computer in the housing 170. Again, the keratometer 212 is arranged to provide more information about the curvature in the central region of the cornea than is provided by most conventional keratometers. The keratometer output relating to the cornea is converted to machine readable form before being output via line 214 to the computer.

In the apparatus used in this method the knurled ring 194 of the beam dimension control means 158 is motorised and the drive motor 196 is controlled by the computer.

The suction cup 206 and arm eyepiece are attached as in the first method, and the nitrogen flow initiated.

The input from line 214 enables the computer to calculate the current shape of the cornea. The operator inputs the desired final shape through a keyboard (not shown) and this is stored in a memory device (RAM) of the computer. The computer then calculates the difference between the current shape and the desired final shape, and the depth of erosion required at each of a series of points on the cornea. Since the depth of erosion obtained is directly related to the number of laser pulses applied, the computer then calculates the number of pulses which should be applied to each point. However, the computer programme is designed so that the number of pulses calculated by the computer is only 75% of the number of pulses actually required to achieve the desired shape, given the laser beam intensity and wavelength used.

From the number of pulses required at each point, the computer calculates what sequence of irradiation areas is required together with the number of pulses of irradiation required for each area. This is calculated on the basis of the difference in the number of pulses required for adjacent points on the cornea. Thus if one area requires 100 pulses more than another, the sequence derived by the computer should include an area which covers the first point but not the second and which is irradiated for 100 pulses.

When the computer has determined the irradiation sequence, it outputs through a printer or a display the measured current corneal profile, the calculated correction required, and its calculated irradiation sequence. These can then be reviewed and confirmed by the surgeon supervising the operation.

After the computer output has been confirmed, the operator inputs to the computer a signal to begin the irradiation sequence. The computer drives the motor 196 to set the area of irradiation to the first area in the sequence The laser is then operated. Computer control enables a faster laser pulse rate to be used, typically 50 Hz.

Preferably the computer calculates from the sequence of irradiation axes a continuous time/beam dimension curve and drives the motor 196 accordingly, as is described with reference to the first method.

At the end of the irradiation sequence, the computer uses the input from the keratometer 212 to calculate the new corneal profile and the correction now required. If all has gone according to plan, 75% of the previously calculated correction has been made. The computer repeats the process described above (including outputting its calculations and awaiting confirmation from the operator) until the calculated correction required falls within predetermined acceptable limits.

The keratomer input is preferably monitored continuously by the computer, so that if any excessive erosion occurs at any time this will be detected and the laser turned off automatically.

If the keratometer input is monitored continuously, the computer may calculate an irradiation sequence to perform the full correction to be made in a single irradiation sequence and control the laser and the beam dimensions accordingly, the keratometer input being used to recalculate and correct the irradiation sequence while it is in progress. In this case, the computer calculates initially a projected time/beam dimension curve. However, if the keratometer input during erosion reveals that the depth of erosion at any point is more than or less than the expected amount, the time/beam dimension curve is recalculated to decrease or increase, respectively, the number of pulses applied to the appropriate area to correct the deviation from the expected amount of erosion.

In the case of removing corneal ulcers, the method of operation of the apparatus are similar, but the object of the erosion is to remove the ulcerous cells with the minimum of reprofiling. Accordingly, the size, shape and number of the pulses of laser energy are controlled with that end in view and the size and shape of the beam may remain constant for all pulses.

The principles of the present invention have been tested by various experiments.

In one series of experiments, batches of 6 to 10 pig or human donor eyes were eroded with varying areas of irradiation, to show corneal reprofiling. In such an experiment, an eye was brought up to the exit aperture of the eyepiece 190 of the apparatus as shown in FIG. 22 (without the suction cup or the measuring device 212. The beam dimension control means was set to provide a large irradiation area and the laser beam pulsed at 5 Hz for 30 seconds. The beam dimension control means was then adjusted to provide a slightly reduced area of irradiation and the laser was pulsed at 5 Hz for a further 30 seconds. The area of irradiation was reduced again, and the procedure repeated to provide concentric rings of increasing depth of erosion.

The eye was then "fixed" chemically to prepare it for electron microscopy. Examination through an electron microscope revealed that there were a series of steps in the surface of the corneal stroma. In different cases the heights of the steps varied, as different pulse energy densities were used. The step heights were in the range of 25 to 1000 nm.

Surprisingly, it was discovered that the depth of corneal stroma eroded per pulse varied in dependence on whether the overlying epithelium layer had been ablated by the laser or removed by some other means before the laser was used. The depth of corneal stroma eroded was greater if the laser had been used to ablate the epithelium. The reason for this is not clear, but it is believed to involve action of the tear film.

The eyepiece of FIG. 22 has also been tested with the suction cup 206 connected to it and attached to the eye. These tests were carried out on rabbit and human donor eyes, and on "phantom" eyes made from gelatin. Only low irradiation intensities were used in these tests, which did not involve experimental ablation.

In order to ensure that the proposed method is suitable for medical uses, experiments to test healing of the eye were performed on monkeys. In these experiments the area of irradiation was kept constant and 3 mm diameter cylindrical recesses were ablated to various depths in the eyes of live monkeys. After six months, two of the monkeys were examined using clinical techniques. Of the four recesses, three were clear. The fourth (which was the deepest at 70 to 100 um deep) was not opaque, but showed a slight sheen.

Electron microscopy showed that the clear eyes had healed with minimal disturbance of the corneal stroma and with good regrowth of the epithelium over the area of the recess. The epithelium had good adhesion and a rigidly oriented basement membrane. The basement membrane in this case was laid down by the cells of the regrown epithelium, which also broke down the pseudo-membrane which had been formed at the corneal surface by the laser. Additionally, the new surface of the stroma had been reorganised to form a Bowman's membrane-like structure.

Background information useful in repeating these experiments may be found in Marshall et al "Photoablative reprofiling of the cornea using an Excimer laser: photorefractive keratectomy", Lasers in Ophthalmology Vol. 1, 1986, pp 21–48.

We claim:

1. A laser system for eroding a surface, said laser system comprising:
   laser means for generating pulses of laser light along a beam path at an energy level, such that the pulses can be absorbed at a surface to induce photoablation;
   support means for aligning a surface relative to the laser means; and
   beam dimension control means disposed along said laser beam path, including optical means for optically varying an area on the surface to which the pulses of laser energy are delivered while maintaining a substantially constant energy per unit area during each pulse.

2. A laser system according to claim 1 and further comprising optical beam-shaping means for varying the shape of the area of the surface to which the pulses are delivered.

3. A laser system according to claim 1 in which the laser means generates from about 1 to about 500 pulses per second.

4. A laser system according to claim 1 in which said control means further comprises beam-shaping means for receiving a laser beam provided by said laser means and for shaping the beam by passage through an aperture, the beam-shaping means being disposed about an optical axis of the laser beam, such that movement along the optical axis varies the cross-sectional area of the beam which passes through the aperture.

5. A laser system according to claim 4 which further comprises a focusing means for focusing an image of the aperture of the beam-shaping means onto the surface to be eroded.

6. A method of eroding a surface by laser energy, said method comprising the steps of:
   aligning a surface with a laser means, which is operable to deliver a beam of photoablative pulses of laser energy along a path to the surface;
   adjusting the size of the area on the surface to which the pulses are delivered; and
   operating a beam dimension control means disposed along said path for optically controlling said beam to deliver pulses of laser energy of variable cross-sectional area to the surface while maintaining a substantially constant energy per unit area during each pulse.

7. A method according to claim 6 in which the shape of the area on the surface to which the pulses are delivered is adjusted in a controlled manner thereby selecting the shape of the area eroded by the pulses.

8. A method according to claim 6 in which the size of the area to be eroded by said pulses is varied in a controlled manner during said step of operating the laser.

9. A method according to claim 6 in which following said step of adjusting the size of the area to be eroded, the size of said area to be eroded is maintained substantially constant during said step of operating the laser.

10. A laser system for eroding and thereby shaping or reprofiling a surface, said laser system comprising:
   support means for aligning a surface to be eroded relative to an optical axis (or vice versa),
   a beam delivery system for relaying energy from a laser light source onto the surface along said optical axis,
   a laser light source, power supply and an associated control circuit for generating pulses of laser energy for application to the surface; and
   beam dimension control means disposed along said optical axis, including optical means for optically controlling the area over which the pulses of laser energy are applied to the surface while maintaining a substantially constant energy per unit area during each pulse, thereby causing greater or lesser ablation of selected regions of the surface.

11. A laser system according to claim 10 for use when the said surface is the surface of an optical element and further comprising:
   a measuring device for measuring a parameter which is a function of surface shape of the optical element;
   means for receiving an input defining a desired value for the parameter;
   comparison means for comparing the measured value of the parameter with the desired value and deriving therefrom a feedback signal; and
   control signal generating circuit means for generating control signals for the laser from the feedback signal obtained from the comparison means, the control signals serving inter alia, to determine the area of the surface to which the laser pulses are applied thereby obtaining the desired value of the parameter of the optical element.

12. A laser system according to claim 10 in which the energy density of the laser pulses applied to the surface is above the threshold value for ablation of corneal tissue and not substantially higher than the saturation level for ablation of corneal tissue.

13. A laser system according to claim 10 in which said beam delivery system comprises a straight-sided-concave optical element for causing beam portions to diverge, leaving an intervening area of reduced beam intensity.

14. A laser system according to claim 10 in which said means for controlling the area comprises an optical stop with first and second zoom systems to the upstream and downstream thereof, said zoom systems being coupled for simultaneous adjustment.

15. A method of eroding a surface of an object, said method comprising the steps of:
   aligning a surface of an object with a laser source which is operable to deliver pulses of laser energy to the surface,
   pulsing the laser source along a path so that light therefrom falls on the surface of the object, and
   controlling the light from the laser with a beam dimension control means disposed along said path so as to optically vary the area over which the light is incident during the emission of a plurality of pulses, thereby selectively exposing areas of the surface to a greater or lesser extent while maintaining a substantially constant energy per unit are during each pulse, and thereby obtaining a desired erosion profile of the surface.

16. A method according to claim 15 in which the laser wavelength is selected so that the laser energy incident on the surface of the object is absorbed by the material forming the surface, so that there is little or no energy remaining to penetrate and affect the material below the surface.

17. A method according to claim 15 in which pulses of energy are directed towards selected overlapping regions of the surface, so that, over a period of time, different regions of the surface are exposed to different quantities of energy from the laser source, so as to produce differential erosion of the surface.

18. A method according to claim 15 in which the energy density of the laser pulses falling on the surface is greater than the threshold for ablation but not substantially greater than the saturation level for ablation of the material of the object.

19. A method according to claim 15 and comprising the further step of inducing a flow of gas over the surface during the erosion process to remove debris arising from the interaction of the laser beam with the surface.

20. A method according to claim 19 in which the gas is nitrogen.

21. A method of eroding an area of a cornea of an eye said method comprising the steps of:
   fixing an eye relative to laser means operable to deliver a beam of photoablative pulses of laser energy along a path to the surface of the cornea;
   varying the area on the surface of the cornea to which the pulses are delivered in a controlled manner; and
   operating a beam dimension control means disposed along said path for optically controlling said beam to deliver pulses of laser to the varied areas of the surface while maintaining a substantially constant energy per unit area during each pulse.

22. A method of removing corneal ulcers comprising steps of:
   fixing an eye relative to laser means operable to deliver a beam of photoablative pulses of laser energy along a path to the surface of the cornea;
   varying the area on the surface of the cornea to which the pulses are delivered in a controlled manner so as to expose the corneal ulcer; and
   operating a beam dimension control means disposed along said path for optically controlling said beam to deliver pulses of laser energy of variable cross-sectional area to the ulcer while maintaining a substantially constant energy per unit area during each pulse.

23. A method of preparing a bed for a corneal transplant in which corneal material is removed by erosion using a method comprising the steps of:
   fixing an eye relative to the laser means to deliver a beam of photoablative pulses of laser energy along a path to the surface of the cornea;
   varying the area on the surface of the cornea to which the pulses are delivered in a controlled manner so as to expose a corneal transplant bed; and
   operating a beam dimension control means disposed along said path for optically controlling said beam to deliver pulses of laser energy of variable cross-sectional area to the transplant bed while maintaining a substantially constant energy per unit area during each pulse.

24. A method of preparing a donor implant for a corneal transplant in which the implant is obtained from a donor cornea by eroding the surrounding area of the donor cornea by a method comprising the steps of:

fixing an eye relative to laser means to deliver a beam of photoablative pulses of laser energy along a path to the surface of the cornea;

varying the area on the surface of the cornea to which the pulses are delivered in a controlled manner so as to expose a region surrounding a donor cornea; and operating a beam dimension control means disposed along said path for optically controlling said beam to deliver pulses of laser energy of variable cross-sectional area to the surrounding region while maintaining a substantially constant energy per unit area during each pulse.

25. A method of correcting ocular disorders by reprofiling a corneal surface of an eye, the method comprising the steps of:

aligning a cornea of an eye with a laser which, in use, generates a beam of laser light capable of photoablating corneal tissue;

pulsing the laser source so that light therefrom propagates along a path and falls intermittently on the surface of the cornea to induce photoablation of a thin surface layer of the cornea within an area of exposure during each pulse;

controlling the light with a beam dimension control means disposed along said path from the laser to optically vary said area of exposure while maintaining a substantially constant energy per unit area during each pulse, whereby a reprofiled corneal surface is obtained as a result of variations in the total energy delivered to selected regions of corneal surface.

26. The method of claim 25 wherein the step of aligning the cornea with the laser further comprises immobilizing the eye by vacuum clamping.

27. The method of claim 25 wherein the step of pulsing the laser source to induce photoablation further comprises delivering ultraviolet light to the surface of the cornea.

28. The method of claim 27 wherein the step of delivering ultraviolet light to the surface of the cornea further comprises delivering ultraviolet light at a wavelength of about 193 nanometers.

29. The method of claim 25 wherein the step of pulsing the laser source to induce photoablation of the cornea further comprises delivering laser light at an energy level ranging from about 0.1 to about 1.0 Joules/cm$^2$.

30. The method of claim 25 wherein the step of controlling the light from the laser further comprises varying the area of exposure to obtain a general flattening of the surface of the cornea and thereby decrease the refractive power of the eye.

31. The method of claim 25 wherein the step of controlling the light from the laser further comprises varying the area of exposure to increase the curvature of the cornea and thereby increase the refractive power of the eye.

32. The method of claim 25 wherein the step of controlling the light from the laser further comprises varying a non-circular area of exposure to correct astigmatisms.

33. The method of claim 25 wherein the method further comprises the step of periodically measuring the curvature of the corneal surface while the area of exposure is being varied and comparing the measured curvature values with expected values in order to provide a feedback-based control of said laser.

34. The method of claim 25 wherein the method further comprises employing a microprocessor which is initially input with a final shape desired, which is also input with measured data as to the extent of reprofiling achieved after a first area is exposed to photoablative light and which outputs control signals which control subsequent exposures.

35. A corneal reprofiling system for modifying the surface of a cornea of an eye, the system comprising:

a laser means generating a beam of pulses of laser light along a path at an energy level, such that the light pulses can be absorbed in a thin surface layer of a cornea of an eye to induce photoablation;

a support means for aligning an eye relative to the laser means; and a beam dimension control means disposed along the path, including a beam-forming optical means for optically varying a area over which the laser light is incident while maintaining a substantially constant energy per unit area during each pulse.

36. The system of claim 35 wherein the laser means generates pulses of ultraviolet laser light at a wavelength of about 193 nanometers.

37. The system of claim 36 wherein the laser means generates pulses of laser light at an energy level ranging from about 1.0 Joules/cm$^2$.

38. The system of claim 35 wherein the support means for aligning an eye relative to the laser means further comprises a vacuum clamp capable of immobilizing an eye.

39. The system of claim 35 wherein the beam-forming optical means further comprises a composite zoom lens arrangement.

40. The system of claim 35 wherein the beam-forming optical means further comprises complementary conical lenses.

41. The system of claim 35 wherein the beam-forming optical means further comprises complementary mirrored surfaces.

42. The system of claim 35 wherein the system further comprises a feedback monitoring means for inspecting the surface which is being exposed to the laser light and for generating control signals to the laser means in response to said inspection of the surface.

43. The system of claim 35 wherein the system further comprises a microprocessor which is initially input with a final shape desired, which also input during the procedure with measured data as to the extent of reprofiling so far achieved, and which outputs control signals which control at least the laser means.

44. The system of claim 35 wherein the system further comprises means for introducing a gaseous flow over the corneal surface during the ablation process to remove debris.

* * * * *

UNITED STATES PATENT AND TRADEMARK OFFICE
CERTIFICATE OF CORRECTION

PATENT NO. : 4,941,093

DATED : July 10, 1990

INVENTOR(S) : Marshall et al.

It is certified that error appears in the above-identified patent and that said Letters Patent is hereby corrected as shown below:

On the title page, 57 Abstract, line 16, "beam dimensional", should read --beam dimension--.

Column 3, line 39, "invention's," should read --invention,--.

Column 3, lines 52-53, "there's by", should read --thereby--.

Column 13, line 58, "can's he", should read --can be--.

Column 16, line 9, "The's", should read --The--.

Column 21, line 50, after the word "shown", insert --)--.

Column 28, line 35, after the word "about", insert -- 0.1 to about--.

Signed and Sealed this

Thirty-first Day of December, 1991

Attest:

HARRY F. MANBECK, JR.

*Attesting Officer*

*Commissioner of Patents and Trademarks*

UNITED STATES PATENT AND TRADEMARK OFFICE
CERTIFICATE OF CORRECTION

PATENT NO. : 4,941,093

DATED : July 10, 1990

INVENTOR(S) : Marshall et al.

It is certified that error appears in the above-identified patent and that said Letters Patent is hereby corrected as shown below:

On the title page in References Cited: U.S. in Patent Documents, before the line beginning "3,941,973 3/1976 Luck, Jr. et al....", insert the lines --3,558,208  1/1971  Hudson ..................... 350/314

3,703,176  11/1972  Vassilliadis et al. ......... 128/394

3,769,963  11/1973  Goldman et al. .............. 128/2 R--.

On the title page in References Cited: U.S. in Patent Documents, before the line beginning "4,409,979 10/1983 Roussel et al. ...", insert the lines --3,982,541  9/1976  L'Esperance, Jr. ............ 128/303.1

4,173,980  11/1979  Curtin ..................... 128/303R 4,266,549  5/1981  Kimura ..................... 128/303.1

4,309,998  1/1982  Aaron nee Rosa et al. ....... 128/303.1

4,326,529  4/1982  Doss et al. ................. 128/303.1

4,381,007  4/1983  Doss ....................... 128/303.1--.

UNITED STATES PATENT AND TRADEMARK OFFICE
CERTIFICATE OF CORRECTION

PATENT NO. : 4,941,093

DATED : July 10, 1990

INVENTOR(S) : Marshall et al.

It is certified that error appears in the above-identified patent and that said Letters Patent is hereby corrected as shown below:

On the title page in References Cited: U.S. in Patent Documents, before the line beginning "4,623,776 11/1986 Buchroeder et al. ...", insert the lines --4,461,294  7/1984  Baron ...................... 128/303.1

4,527,043  7/1985  Hashiura et al. ............. 219/121

4,538,608  9/1985  L'Esperance, Jr. ............ 128/303.1--.

On the title page in References Cited: U.S. in Patent Documents, after the line beginning "4,665,913 5/1987 L'Esperance, Jr. ...", insert the lines --4,669,466  6/1987  L'Esperance ................ 128/303.1

4,686,979  8/1987  Gruen et al. ............... 128/303R 4,729,372  3/1988  L'Esperance, Jr. ........... 128/303.1

4,732,214  3/1988  L'Esperance, Jr. ........... 128/303.1

UNITED STATES PATENT AND TRADEMARK OFFICE
CERTIFICATE OF CORRECTION

PATENT NO. : 4,941,093                        Page 3 of 6

DATED : July 10, 1990

INVENTOR(S) : Marshall et al.

It is certified that error appears in the above-identified patent and that said Letters Patent is hereby corrected as shown below:

FOREIGN PATENT DOCUMENTS 0 110 060    9/1983  European Patent Office 0 152 686   12/1984  European Patent Office 3,148,748   12/1981  Germany 3,535,972    9/1987  Germany 3,535,073    9/1987  Germany

WO86/045000  8/1986  PCT

OTHER PUBLICATIONS

Fine et al., "Preliminary Observations on Ocular Effects...", Vol. 64, No. 2, American Journal of Ophthalmology, pp. 209-222 (August 1967)

Beckman et al., "Limbectomies, Keratectomies, and Keratostomies Performed...", Vol. 71, American Journal of Ophthalmology, pp. 1277-1283 (June 1971)

UNITED STATES PATENT AND TRADEMARK OFFICE
CERTIFICATE OF CORRECTION

PATENT NO. : 4,941,093

DATED : July 10, 1990

INVENTOR(S) : Marshall et al.

It is certified that error appears in the above-identified patent and that said Letters Patent is hereby corrected as shown below:

Mainster, "Ophthalmic Applications of Infrared Lasers--Thermal considerations", Vol. 18, No. 4, Invst. Ophthal. and Vis. Sci., pp. 414-420 (1979)

Peyman et al., "Modification of Rabbit Corneal Curvature with Use of Carbon Dioxide Laser Burns", Vol. 11, No. 5, Ophthalmic Surgery, pp. 325-329 (May 1980)

Keates et al., "Carbon Dioxide Laser Beam Control for Corneal Surgery", Vol. 12, No. 2, Ophthalmic Surgery, pp. 117-122 (February 1981)

Girard, "Refractive Keratoplasty", Vol. 2, Corneal Surgery, pp. 142-171 (1981)

Taboada et al., "Response of the Corneal Epithelium to KrF Excimer Laser Pulses", Vol. 40, Health Physics, pp. 677-683 (May 1981)

Chetverukhin et al., "Refraction Thermokeratoplasty and Laser Keratoplasty", Vestn. Oftal., pp. 67-69 (USSR 1982)

UNITED STATES PATENT AND TRADEMARK OFFICE
CERTIFICATE OF CORRECTION

PATENT NO. : 4,941,093

DATED : July 10, 1990

INVENTOR(S) : Marshall et al.

It is certified that error appears in the above-identified patent and that said Letters Patent is hereby corrected as shown below:

Srinivasan et al., "Far-UV Photoetching of Organic Material", Laser Focus (May 1983)

Srinivasan, "Kinetics of the Ablative Photodecomposition of Organic Polymers...", Vol. B1, J. of Vac. Sci. Technol., pp. 923-926 (1983)

Srinivasan, "Action of Far-Ultraviolet Light on Organic Polymer Films...", pp. 12-14 (October 1983)

Trokel, et al., "Excimer Laser Surgery of the Cornea", Vol. 96, American Journal of Ophthalmology, pp. 710-715 (1983)

Galbavy, "Use of Diamond Knives in Ocular Surgery", Vol. 15, No. 3, Ophthalmic Surgery, pp. 203-205 (March 1984)

Puliafito et al., "Excimer Laser Ablation of the Cornea and Lens", Vol. 92, No. 6, Ophthalmology, pp. 741-748 (June 1985)

UNITED STATES PATENT AND TRADEMARK OFFICE
CERTIFICATE OF CORRECTION

PATENT NO. : 4,941,093

DATED : July 10, 1990

INVENTOR(S) : Marshall et al.

It is certified that error appears in the above-identified patent and that said Letters Patent is hereby corrected as shown below:

L'Esperance, Jr., "New Laser Systems and Their Potential Clinical Usefulness", Trans. New Orleans Acad. of Ophthalmol., pp. 182-209 (1985)

L'Esperance, Jr., "Current Status of Ophtalmic Photovaporization Therapy", Trans. New Orleans Acad. of Ophthalmol., pp. 231-255 (1985)

O'hara et al., Vol. 11, IBM Technical Disclosure Bulletin, pp. 1168-69 (1969)

Binder et al., "Refractive Keratoplasty", Vol. 100, Arch. Ophthalmol., pp. 802-806 (1982)--.

Signed and Sealed this

Twenty-eighth Day of July, 1992

Attest:

DOUGLAS B. COMER

Attesting Officer        Acting Commissioner of Patents and Trademarks

UNITED STATES PATENT AND TRADEMARK OFFICE

CERTIFICATE EXTENDING PATENT TERM
UNDER 35 U.S.C. § 156

PATENT NO.      :   4,941,093

ISSUED          :   July 10, 1990

INVENTOR(S)     :   John Marshall et al.

PATENT OWNER :   Summit Technology, Inc.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 609 days from the original expiration date of the patent, July 10, 2007, with all rights pertaining thereto as provided by 35 U.S.C. § 156(b).

I have caused the seal of the Patent and Trademark Office to be affixed this 31st day of May 1996.

Bruce A. Lehman
Assistant Secretary of Commerce and
Commissioner of Patents and Trademarks